US011827908B2

(12) United States Patent
Ohmuro

(10) Patent No.: US 11,827,908 B2
(45) Date of Patent: *Nov. 28, 2023

(54) POLYPEPTIDE HAVING LUCIFERASE ACTIVITY

(71) Applicant: SHIMADZU CORPORATION, Kyoto (JP)

(72) Inventor: Yuki Ohmuro, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/550,495

(22) Filed: Dec. 14, 2021

(65) Prior Publication Data

US 2022/0259575 A1  Aug. 18, 2022

(30) Foreign Application Priority Data

Feb. 12, 2021 (JP) ................. 2021-021069
Dec. 8, 2021 (JP) ................. 2021-199158

(51) Int. Cl.
| C12N 15/62 | (2006.01) |
| C12N 9/02 | (2006.01) |
| C12Q 1/26 | (2006.01) |
| G01N 21/64 | (2006.01) |
| C12N 15/88 | (2006.01) |

(52) U.S. Cl.
CPC ........... *C12N 9/0069* (2013.01); *C12N 15/62* (2013.01); *C12N 15/88* (2013.01); *C12Q 1/26* (2013.01); *C12Y 113/12007* (2013.01); *G01N 21/6428* (2013.01); *C07K 2319/61* (2013.01); *C12N 2800/10* (2013.01)

(58) Field of Classification Search
CPC .... G01N 33/535; G01N 21/76; G01N 33/543; C12N 15/09; C12Q 1/26; C07K 15/09
See application file for complete search history.

(56) References Cited

U.S. PATENT DOCUMENTS

| 10,214,766 | B2* | 2/2019 | Kim ...................... C12Y 113/12 |
| 10,533,231 | B2* | 1/2020 | Kim ........................ C07K 14/72 |
| 2014/0242574 | A1 | 8/2014 | Inouye et al. |
| 2015/0284813 | A1* | 10/2015 | Kim ...................... G01N 33/535 435/254.2 |
| 2016/0281129 | A1* | 9/2016 | Kim ...................... C07D 487/04 |
| 2018/0265850 | A1 | 9/2018 | Kim |

FOREIGN PATENT DOCUMENTS

| JP | 3048466 | 3/2000 |
| JP | 2014-100137 | 6/2014 |
| JP | 2018-126127 | 8/2018 |
| JP | 2018-126128 | 8/2018 |
| WO | 2017/057752 | 4/2017 |

OTHER PUBLICATIONS

U.S. Appl. No. 17/748,727 filed May 19, 2022 in the Name of Yuki Ohmuro.
NanoBit® PPI Starter Systems <https://www.promegajp/products/protein-interactions/live-cell-protein-interactions/nanobit-ppi-starter-systems/?catNum=N2014>*Japanese <https://www.promega.jp/en/products/protein-interactions/live-cell-protein-interactions/nanobit-ppi-starter-systems/?catNum=N2014&cs=y>, with English translation.
Remy, I., et al., "A highly sensitive protein-protein interaction assay based on Gaussia luciferase", Nature Methods vol. 3 No. 12, Dec. 2006, pp. 977-979.
Kricka et al., "Chemiluminescent Methods for Detecting and Quantitating Enzyme Activity", Methods in Enzymology, vol. 305 (2000) pp. 370-390.
Hamilton et al., "Clinical Evaluation of the ZstatFlu-II Test: a Chemiluminescent Rapid Diagnostic Test for Influenza Virus", Journal of Clinical Microbiology, vol. 40, No. 7, (2002), pp. 2331-2334.
Ho et al., "Reporter Enzyme Inhibitor Study to Aid Assembly of Orthogonal Reporter Gene Assays", ACS Chem. Biol. (2013), vol. 8, pp. 1009-1017.
Auld et al., "Characterization and Use of TurboLuc Luciferase as a Reporter for High-Throughput Assays", Biochemistry (2018), vol. 57, pp. 4700-4706.
Secreted Luciferase Reporter Assay—Takara Bio Inc. http://catalog.takara-bio.co.jp/product/basic_info.php?unitid=U100005159 with machine translation inserted in red font.
Hall et al., "Engineered Luciferase Reporter from a Deep Sea Shrimp Utilizing a Novel Imidazopyrazinone Substrate", ACS Chem. Biol. (2012) vol. 7, pp. 1848-1857.
Kim et al., "Fabrication of a New Lineage of Artificial Luciferases from Natural Luciferase Pools", ACS Comb. Sci. (2017), vol. 19, pp. 594-599.
Markova et al., "Shining Light on the Secreted Luciferases of Marine Copepods: Current Knowledge and Applications", Photochemistry and Photobiology, (2019), vol. 95, pp. 705-721.
Hunt et al., "Truncated Variants of *Gaussia* Luciferase with Tyrosine Linker for Site-Specific Bioconjugate Applications", Scientific Reports 6:26814 DOI: 10.1038/srep26814 (2016).
Takenaka et al., "Two forms of secreted and thermostable luciferases from the marine copepod crustacean, *Metridia pacifica*", Gene 425 (2008) pp. 28-35.

(Continued)

*Primary Examiner* — Maryam Monshipouri
(74) *Attorney, Agent, or Firm* — Wenderoth, Lind & Ponack, L.L.P.

(57) ABSTRACT

A novel luciferase with a small molecular weight is provided. A polypeptide with luciferase activity comprising an amino acid sequence (A) or (B) is provided:

(A) an amino acid sequence as set forth in SEQ ID NO: 1 with deletion of amino acid residues at positions 1 to 69 and 204 to 221; or (B) an amino acid sequence as set forth in SEQ ID NO: 1 with deletion of amino acid residues at positions 1 to 69 and deletion or substitution of at least one of amino acid residues 146 to 156.

7 Claims, 26 Drawing Sheets

Specification includes a Sequence Listing.

(56) References Cited

OTHER PUBLICATIONS

Kim and Izumi, "Functional artificial luciferases as an optical readout for bioassays", Biochemical and Biophysical Research Communication 448 (2014) pp. 418-423.
Kim et al., "Creation of Artificial Luciferases for Bioassays", Bioconjugate Chem. (2013), vol. 24, pp. 2067-2075.
Ooe et al., "Properties of the enzyme luciferase", Kogaku to Seibutsu (Science and Organisms) vol. 52, No. 1, (2014) pp. 59-60, machine translation.
TurboLuc Luciferase One-Step Glow Assay Kit—Thermo Fisher Scientific. 2015. https://www.thermofisher.com/order/catalog/product/88263#/88263ha.

* cited by examiner

FIG.2

Comparison of amino acid sequences of picALuc30 and picALuc16

```
                                                                              54
ALuc30 wt    1 HHHHHHHDIVGVEGKFGTTDLETDLFTIVEDMNVISRDTDVDANRADRGRRG KLPGKKL
ALuc16 wt    1 PTENKDDIDIVGVEGKFGTTDLETDLFTIVEDMNVISRDTDVDANRADRGRRG KLPGKKL
                      *  ************************************************

ALuc30 wt   61 PLEVLKELEANAQKAGCTRGCLICLSHIKCTAKMKKWLPGRCESWEGDKETGQGGIGEAI
ALuc16 wt   61 PLEVLKELEANAQKAGCTRGCLICLSHIKCTAKMKKWLPGRCESWEGDKETGQGGIGEAI
               ************************************************************

122                                          175
ALuc30 wt  121 VDIPEIPGFKELAPMEQFIAQVDLCADCTTGQCLKGLANVKCSALLKKWLPSRCAGFADKI
ALuc16 wt  121 VDIPEIPGFKDLEPMEQFIAQVDLCVDCTTGQCLKGLANVKCSDLLKKWLPSRCATFASKI
               **********  * ********** *********** ****** *********** ** *

193
ALuc30 wt  181 QAQVDTIKGAGGS
ALuc16 wt  181 QAQVDKIKGAGGS
               ***** *******
```

☐ : picALuc sequence
96% identity (picALuc sequence)

FIG.3

Comparison of amino acid sequences of picALuc30 and picALuc48

```
ALuc30 wt    1 HHHHHHHHDIVGVEGKFGTTDLETDLFTIVEDMNVISRDTDVDANRADRGRRGK--LPGK   54
ALuc48 wt    1 PTENKDDIDIVGVEGKFGTTDLETDLFTIVEDMNVISRDTDVDANRADRGRRGHGGLPGK   54
               *         ************************************* ***   ****

ALuc30 wt   59 KLPLEVLKELEANAQKAGCTRGCLICLSHIKCTAKMKKWLPGRCESWEGDKETGQGGI-G
ALuc48 wt   61 KMPLEVLLELELANAQRAGCTRGCLICLSKIKCTAKMKKWLPGRCESWAGDKETGQGGITE
               * ****  *** ***** ************ ****************** *********

ALuc30 wt  118 EAIVDIPEIPGFKELAPMEQFIAQVDLCADDTTGCLKGLANVKCSALLKKWLPSRCAGFA  175
ALuc48 wt  121 EETVDIPEIPGFKDLEPMEQFIAQVDLCVDDTTGCLKGLANVKCSDLLKKWLPSRCATFA  178
               *  ********* * ************ **************** ***********  *

ALuc30 wt  178 DKIQAQVDTIKGAGGS  193
ALuc48 wt  181 SKIQAQVDKIKGAGGS  196
               ******* *******
```

☐ : picALuc sequence
85% identity (picALuc sequence)

FIG.4

Comparison of amino acid sequences of picALuc48 and picALuc16

```
ALuc48 wt    1 PTENKDDIDIVGVEGKFGTTDLETDLFTIVEDMNVISRDTDVDANRADRGRRGHGGLPGK    54
ALuc16 wt    1 PTENKDDIDIVGVEGKFGTTDLETDLFTIVEDMNVISRDTDVDANRADRGRRGK--LPGK    54
               ********************************************* **

ALuc48 wt   61 KMPLEVLLELEANAQRAGCTRGCLICLSKIKCTAKMKKWLPGRCESWAGDKETGQGGITE
ALuc16 wt   59 KLPLEVLKELEANAQKAGCTRGCLICLSHIKCTAKMKKWLPGRCESWEGDKETGQGGIG-
               * ***** ******* ****************** *********** *********

ALuc48 wt  121 EETVDIPEIPGFKDLEPMEQFIAQVDLCVDCTTGCLKGLANVKCSDLLKKWLPSRCATFA   178
ALuc16 wt  118 EAIVDIPEIPGFKDLEPMEQFIAQVDLCVDCTTGCLKGLANVKCSDLLKKWLPSRCATFA   175
               * ********************************************************

ALuc48 wt  181 SKIQAQVDKIKGAGGS                                             196
ALuc16 wt  178 SKIQAQVDKIKGAGGS                                             193
               ****************
```

☐ : picALuc sequence
☐ 90% identity (picALuc sequence)

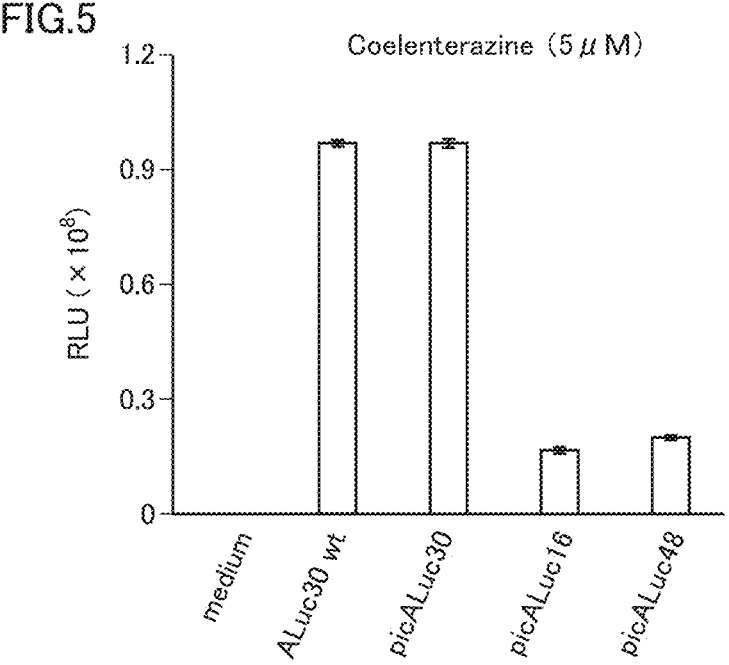

SEQUENCE LISTING

```
<160> NUMBER OF SEQ ID NOS: 75

<210> SEQ ID NO 1
<211> LENGTH: 221
<212> TYPE: PRT
<213> ORGANISM: Artificial Sequence
<220> FEATURE:
<223> OTHER INFORMATION: ALucCM (common artificial luciferase)
<220> FEATURE:
<221> NAME/KEY: misc_feature
<222> LOCATION: (3)..(7)
<223> OTHER INFORMATION: Xaa(3)=any a.a. Xaa(5)=hydrophilic a.a. Xaa(4,
```

```
      6,7)=aliphatic a.a.
<220> FEATURE:
<221> NAME/KEY: misc_feature
<222> LOCATION: (10)..(11)
<223> OTHER INFORMATION: Xaa(10,11)=aliphatic a.a.
<220> FEATURE:
<221> NAME/KEY: misc_feature
<222> LOCATION: (13)..(13)
<223> OTHER INFORMATION: Xaa(13)=hydrophobic a.a.
<220> FEATURE:
<221> NAME/KEY: misc_feature
<222> LOCATION: (15)..(16)
<223> OTHER INFORMATION: Xaa(16)=hydrophobic a.a. Xaa(15)=aliphatic a.a.
<220> FEATURE:
<221> NAME/KEY: misc_feature
<222> LOCATION: (20)..(29)
<223> OTHER INFORMATION: Xaa(20,21,24-29)=any a.a. Xaa(22,23)=any or no
      a.a.
<220> FEATURE:
<221> NAME/KEY: misc_feature
<222> LOCATION: (31)..(35)
<223> OTHER INFORMATION: Xaa(31,32,35)=any a.a. Xaa(33,34)=aliphatic
      a.a.
<220> FEATURE:
<221> NAME/KEY: misc_feature
<222> LOCATION: (37)..(37)
<223> OTHER INFORMATION: Xaa(37)=any a.a.
<220> FEATURE:
<221> NAME/KEY: misc_feature
<222> LOCATION: (39)..(41)
<223> OTHER INFORMATION: Xaa(39,40)=aliphatic or no a.a. Xaa(41)=
      aliphatic a.a.
<220> FEATURE:
<221> NAME/KEY: misc_feature
<222> LOCATION: (62)..(69)
<223> OTHER INFORMATION: Xaa(64-66,69)=any a.a. Xaa(67)=hydrophilic a.a.
      Xaa(63,68)=aliphatic a.a. Xaa(62)=negative a.a.
<220> FEATURE:
<221> NAME/KEY: misc_feature
<222> LOCATION: (72)..(78)
<223> OTHER INFORMATION: Xaa(76,77)=any or no a.a. Xaa(75)=hydrophilic
      a.a. Xaa(74)=aliphatic or no a.a. Xaa(78)=aliphatic a.a.
      Xaa(72,73)=positive or no a.a.
<220> FEATURE:
<221> NAME/KEY: misc_feature
<222> LOCATION: (83)..(83)
<223> OTHER INFORMATION: Xaa(83)=aliphatic a.a.
<220> FEATURE:
<221> NAME/KEY: misc_feature
<222> LOCATION: (85)..(86)
<223> OTHER INFORMATION: Xaa(85,86)=any a.a.
<220> FEATURE:
<221> NAME/KEY: misc_feature
<222> LOCATION: (89)..(90)
<223> OTHER INFORMATION: Xaa(89,90)=any a.a.
<220> FEATURE:
<221> NAME/KEY: misc_feature
<222> LOCATION: (97)..(97)
<223> OTHER INFORMATION: Xaa(97)=positive a.a.
<220> FEATURE:
<221> NAME/KEY: misc_feature
<222> LOCATION: (101)..(101)
<223> OTHER INFORMATION: Xaa(101)=hydrophilic a.a.
<220> FEATURE:
<221> NAME/KEY: misc_feature
<222> LOCATION: (110)..(110)
<223> OTHER INFORMATION: Xaa(110)=positive a.a.
<220> FEATURE:
<221> NAME/KEY: misc_feature
<222> LOCATION: (119)..(119)
<223> OTHER INFORMATION: Xaa(119)=hydrophilic a.a.
<220> FEATURE:
<221> NAME/KEY: misc_feature
<222> LOCATION: (129)..(129)
<223> OTHER INFORMATION: Xaa(129)=any a.a.
<220> FEATURE:
<221> NAME/KEY: misc_feature
<222> LOCATION: (137)..(137)
<223> OTHER INFORMATION: Xaa(137)=aliphatic a.a.
```

```
<220> FEATURE:
<221> NAME/KEY: misc_feature
<222> LOCATION: (140)..(144)
<223> OTHER INFORMATION: Xaa(140)=any or no a.a. Xaa(141-144)=any a.a.
<220> FEATURE:
<221> NAME/KEY: misc_feature
<222> LOCATION: (148)..(151)
<223> OTHER INFORMATION: Xaa(148-151)=any or no a.a.
<220> FEATURE:
<221> NAME/KEY: misc_feature
<222> LOCATION: (159)..(161)
<223> OTHER INFORMATION: Xaa(159,161)=any a.a. Xaa(160)=aliphatic a.a.
<220> FEATURE:
<221> NAME/KEY: misc_feature
<222> LOCATION: (174)..(174)
<223> OTHER INFORMATION: Xaa(174)=hydrophobic a.a.
<220> FEATURE:
<221> NAME/KEY: misc_feature
<222> LOCATION: (188)..(188)
<223> OTHER INFORMATION: Xaa(188)=any a.a.
<220> FEATURE:
<221> NAME/KEY: misc_feature
<222> LOCATION: (191)..(191)
<223> OTHER INFORMATION: Xaa(191)=any a.a.
<220> FEATURE:
<221> NAME/KEY: misc_feature
<222> LOCATION: (202)..(203)
<223> OTHER INFORMATION: Xaa(202)=any a.a. Xaa(203)=aliphatic a.a.
<220> FEATURE:
<221> NAME/KEY: misc_feature
<222> LOCATION: (206)..(206)
<223> OTHER INFORMATION: Xaa(206)=any a.a.
<220> FEATURE:
<221> NAME/KEY: misc_feature
<222> LOCATION: (211)..(211)
<223> OTHER INFORMATION: Xaa(211)=negative a.a.
<220> FEATURE:
<221> NAME/KEY: misc_feature
<222> LOCATION: (214)..(214)
<223> OTHER INFORMATION: Xaa(211)=hydrophilic a.a.
<220> FEATURE:
<221> NAME/KEY: misc_feature
<222> LOCATION: (218)..(218)
<223> OTHER INFORMATION: Xaa(218)=hydrophobic a.a.

<400> SEQUENCE: 1

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Xaa Xaa Xaa Xaa Asp Xaa Xaa
            20                  25                  30

Xaa Xaa Xaa Gly Xaa Phe Xaa Xaa Xaa Asp Leu Glu Thr Asp Leu Phe
        35                  40                  45

Thr Ile Val Glu Asp Met Asn Val Ile Ser Arg Asp Thr Xaa Xaa Xaa
    50                  55                  60

Xaa Xaa Xaa Xaa Xaa Arg Gly Xaa Xaa Xaa Xaa Xaa Xaa Xaa Pro Gly
65                  70                  75                  80

Lys Lys Xaa Pro Xaa Xaa Val Leu Xaa Xaa Leu Glu Ala Asn Ala Gln
                85                  90                  95

Xaa Ala Gly Cys Xaa Arg Gly Cys Leu Ile Cys Leu Ser Xaa Ile Lys
            100                 105                 110

Cys Thr Ala Lys Met Lys Xaa Trp Leu Pro Gly Arg Cys Glu Ser Trp
        115                 120                 125

Xaa Gly Asp Lys Glu Thr Gly Gln Xaa Gly Ile Xaa Xaa Xaa Xaa Xaa
    130                 135                 140

Val Asp Ile Xaa Xaa Xaa Xaa Pro Glu Ile Pro Gly Phe Lys Xaa Xaa
145                 150                 155                 160

Xaa Pro Met Glu Gln Phe Ile Ala Gln Val Asp Leu Cys Xaa Asp Cys
                165                 170                 175
```

```
Thr Thr Gly Cys Leu Lys Gly Leu Ala Asn Val Xaa Cys Ser Xaa Leu
            180                 185                 190

Leu Lys Lys Trp Leu Pro Ser Arg Cys Xaa Xaa Phe Ala Xaa Lys Ile
        195                 200                 205

Gln Ala Xaa Val Asp Xaa Ile Lys Gly Xaa Gly Gly Ser
    210                 215                 220

<210> SEQ ID NO 2
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 2

Pro Thr Glu Asn Lys Asp Asp Ile
1               5

<210> SEQ ID NO 3
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 3

Ala Thr Ile Asn Glu Glu Asp Ile
1               5

<210> SEQ ID NO 4
<211> LENGTH: 10
<212> TYPE: PRT
<213> ORGANISM: Artificial Sequence
<220> FEATURE:
<223> OTHER INFORMATION: ALuc partial sequence

<400> SEQUENCE: 4

Ala Thr Ile Asn Glu Asn Phe Glu Asp Ile
1               5                   10

<210> SEQ ID NO 5
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 5

His His His His His His His His
1               5

<210> SEQ ID NO 6
<211> LENGTH: 7
<212> TYPE: PRT
<213> ORGANISM: Artificial Sequence
<220> FEATURE:
<223> OTHER INFORMATION: ALuc partial sequence

<400> SEQUENCE: 6

Glu Lys Leu Ile Ser Glu Glu
1               5

<210> SEQ ID NO 7
<211> LENGTH: 8
<212> TYPE: PRT
```

```
<213> ORGANISM: Artificial Sequence
<220> FEATURE:
<223> OTHER INFORMATION: ALuc partial sequence

<400> SEQUENCE: 7

Met Met Tyr Pro Tyr Asp Val Pro
1               5

<210> SEQ ID NO 8
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 8

Met Met Asp Tyr Lys Asp Asp Asp
1               5

<210> SEQ ID NO 9
<211> LENGTH: 5
<212> TYPE: PRT
<213> ORGANISM: Artificial Sequence
<220> FEATURE:
<223> OTHER INFORMATION: ALuc partial sequence

<400> SEQUENCE: 9

Thr Glu Glu Glu Thr
1               5

<210> SEQ ID NO 10
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 10

Gly Glu Ala Ile
1

<210> SEQ ID NO 11
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 11

Val Gly Ala Ile
1

<210> SEQ ID NO 12
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 12

Gly Val Leu Gly
1

<210> SEQ ID NO 13
<211> LENGTH: 209
<212> TYPE: PRT
<213> ORGANISM: Artificial Sequence
```

<220> FEATURE:
<223> OTHER INFORMATION: ALuc10

<400> SEQUENCE: 13

Met Met Glu Ile Gln Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asn Leu Ala Asn Ser
        50                  55                  60

Asp Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                85                  90                  95

Cys Leu Ile Cys Leu Ser His Ile Lys Cys Thr Ala Lys Met Lys Lys
            100                 105                 110

Trp Leu Pro Gly Arg Cys Glu Ser Trp Glu Gly Asp Lys Glu Thr Gly
        115                 120                 125

Gln Gly Gly Ile Gly Glu Ala Ile Val Asp Ile Pro Glu Ile Pro Gly
    130                 135                 140

Phe Lys Asp Leu Glu Pro Met Glu Gln Phe Ile Ala Gln Val Asp Leu
145                 150                 155                 160

Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205

Ser

<210> SEQ ID NO 14
<211> LENGTH: 209
<212> TYPE: PRT
<213> ORGANISM: Artificial Sequence
<220> FEATURE:
<223> OTHER INFORMATION: ALcu15

<400> SEQUENCE: 14

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                85                  90                  95

Cys Leu Ile Cys Leu Ser His Ile Lys Cys Thr Ala Lys Met Lys Lys
            100                 105                 110

Trp Leu Pro Gly Arg Cys Glu Ser Trp Glu Gly Asp Lys Glu Thr Gly
        115                 120                 125

```
Gln Gly Gly Ile Gly Glu Ala Ile Val Asp Ile Pro Glu Ile Pro Gly
            130                 135                 140
Phe Lys Asp Leu Glu Pro Met Glu Gln Phe Ile Ala Gln Val Asp Leu
145                 150                 155                 160
Cys Val Asp Cys Thr Thr Gly Cys Leu Lys Gly Leu Ala Asn Val Lys
                165                 170                 175
Cys Ser Asp Leu Leu Lys Lys Trp Leu Pro Ser Arg Cys Ala Thr Phe
            180                 185                 190
Ala Ser Lys Ile Gln Ala Gln Val Asp Lys Ile Lys Gly Ala Gly Gly
                195                 200                 205
Ser

<210> SEQ ID NO 15
<211> LENGTH: 212
<212> TYPE: PRT
<213> ORGANISM: Artificial Sequence
<220> FEATURE:
<223> OTHER INFORMATION: ALuc16

<400> SEQUENCE: 15

Met Met Gly Ile Lys Val Leu Phe Ala Leu Ile Cys Phe Ala Leu Val
1               5                   10                  15
Gln Ala Asn Pro Thr Glu Asn Lys Asp Asp Ile Asp Ile Val Gly Val
                20                  25                  30
Glu Gly Lys Phe Gly Thr Thr Asp Leu Glu Thr Asp Leu Phe Thr Ile
            35                  40                  45
Val Glu Asp Met Asn Val Ile Ser Arg Asp Thr Asp Val Asp Ala Asn
50                  55                  60
Arg Ala Asp Arg Gly Arg Arg Gly Lys Leu Pro Gly Lys Lys Leu Pro
65                  70                  75                  80
Leu Glu Val Leu Lys Glu Leu Glu Ala Asn Ala Gln Lys Ala Gly Cys
                85                  90                  95
Thr Arg Gly Cys Leu Ile Cys Leu Ser His Ile Lys Cys Thr Ala Lys
            100                 105                 110
Met Lys Lys Trp Leu Pro Gly Arg Cys Glu Ser Trp Glu Gly Asp Lys
        115                 120                 125
Glu Thr Gly Gln Gly Gly Ile Gly Glu Ala Ile Val Asp Ile Pro Glu
    130                 135                 140
Ile Pro Gly Phe Lys Asp Leu Glu Pro Met Glu Gln Phe Ile Ala Gln
145                 150                 155                 160
Val Asp Leu Cys Val Asp Cys Thr Thr Gly Cys Leu Lys Gly Leu Ala
                165                 170                 175
Asn Val Lys Cys Ser Asp Leu Leu Lys Lys Trp Leu Pro Ser Arg Cys
            180                 185                 190
Ala Thr Phe Ala Ser Lys Ile Gln Ala Gln Val Asp Lys Ile Lys Gly
        195                 200                 205
Ala Gly Gly Ser
    210

<210> SEQ ID NO 16
<211> LENGTH: 212
<212> TYPE: PRT
<213> ORGANISM: Artificial Sequence
<220> FEATURE:
<223> OTHER INFORMATION: ALuc17

<400> SEQUENCE: 16
```

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Met Pro Gly Lys Lys Leu Pro
65                  70                  75                  80

Lys Ala Val Leu Ile Glu Leu Glu Ala Asn Ala Gln Lys Ala Gly Cys
                85                  90                  95

His Arg Gly Cys Leu Ile Cys Leu Ser His Ile Lys Cys Thr Ala Lys
            100                 105                 110

Met Lys Glu Trp Leu Pro Gly Arg Cys Glu Ser Trp Gly Gly Asp Lys
        115                 120                 125

Glu Thr Gly Gln Ala Gly Ile Val Gly Ala Ile Val Asp Ile Pro Glu
    130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
    210

<210> SEQ ID NO 17
<211> LENGTH: 215
<212> TYPE: PRT
<213> ORGANISM: Artificial Sequence
<220> FEATURE:
<223> OTHER INFORMATION: ALuc18

<400> SEQUENCE: 17

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly His Gly Leu Pro Gly Lys Lys
65                  70                  75                  80

Met Pro Leu Glu Val Leu Leu Glu Leu Glu Ala Asn Ala Gln Arg Ala
                85                  90                  95

Gly Cys Thr Arg Gly Cys Leu Ile Cys Leu Ser Lys Ile Lys Cys Thr
            100                 105                 110

Ala Lys Met Lys Lys Trp Leu Pro Gly Arg Cys Glu Ser Trp Ala Gly
        115                 120                 125

Asp Lys Glu Thr Gly Gln Gly Gly Ile Thr Glu Glu Thr Val Asp
    130                 135                 140
```

Ile Pro Glu Ile Pro Gly Phe Lys Asp Leu Glu Pro Met Glu Gln Phe
145                 150                 155                 160

Ile Ala Gln Val Asp Leu Cys Val Asp Cys Thr Thr Gly Cys Leu Lys
                165                 170                 175

Gly Leu Ala Asn Val Lys Cys Ser Asp Leu Leu Lys Lys Trp Leu Pro
            180                 185                 190

Ser Arg Cys Ala Thr Phe Ala Ser Lys Ile Gln Ala Gln Val Asp Lys
        195                 200                 205

Ile Lys Gly Ala Gly Gly Ser
    210                 215

<210> SEQ ID NO 18
<211> LENGTH: 217
<212> TYPE: PRT
<213> ORGANISM: Artificial Sequence
<220> FEATURE:
<223> OTHER INFORMATION: ALuc19

<400> SEQUENCE: 18

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
50                  55                  60

Arg Ala Asp Arg Gly Arg Gly Arg Lys Leu Pro Gly Lys Lys Leu
65                  70                  75                  80

Pro Lys Glu Val Leu Lys Ile Leu Glu Ala Asn Ala Gln Arg Ala Gly
                85                  90                  95

Cys His Arg Gly Cys Leu Ile Cys Leu Ser His Ile Lys Cys Thr Ala
            100                 105                 110

Lys Met Lys Gln Trp Leu Pro Gly Arg Cys Glu Ser Trp Glu Gly Asp
        115                 120                 125

Lys Glu Thr Gly Gln Gly Gly Ile Gly Gly Pro Ile Val Asp Ile Gly
    130                 135                 140

Val Leu Gly Pro Glu Ile Pro Gly Phe Lys Asp Leu Glu Pro Met Glu
145                 150                 155                 160

Gln Phe Ile Ala Gln Val Asp Leu Cys Val Asp Cys Thr Thr Gly Cys
                165                 170                 175

Leu Lys Gly Leu Ala Asn Val Lys Cys Ser Asp Leu Leu Lys Lys Trp
            180                 185                 190

Leu Pro Ser Arg Cys Ala Thr Phe Ala Ser Lys Ile Gln Ala Gln Val
        195                 200                 205

Asp Lys Ile Lys Gly Ala Gly Gly Ser
    210                 215

<210> SEQ ID NO 19
<211> LENGTH: 212
<212> TYPE: PRT
<213> ORGANISM: Artificial Sequence
<220> FEATURE:
<223> OTHER INFORMATION: ALuc21

<400> SEQUENCE: 19

Met Met Gly Ile Lys Val Leu Phe Ala Leu Ile Cys Phe Ala Leu Val

```
                1               5                      10                        15
            Gln Ala Asn Ala Thr Ile Asn Glu Glu Asp Ile Asp Leu Val Ala Ile
                            20                  25                  30

Gly Gly Ser Phe Ala Thr Thr Asp Leu Glu Thr Asp Leu Phe Thr Ile
                        35                  40                  45

Val Glu Asp Met Asn Val Ile Ser Arg Asp Thr Asp Val Asp Ala Asn
                50                  55                  60

Arg Ala Asp Arg Gly Arg Gly Lys Leu Pro Gly Lys Lys Leu Pro
            65                  70                  75                  80

Leu Glu Val Leu Lys Glu Leu Glu Ala Asn Ala Gln Lys Ala Gly Cys
                            85                  90                  95

Thr Arg Gly Cys Leu Ile Cys Leu Ser His Ile Lys Cys Thr Ala Lys
                            100                 105                 110

Met Lys Lys Trp Leu Pro Gly Arg Cys Glu Ser Trp Glu Gly Asp Lys
                            115                 120                 125

Glu Thr Gly Gln Gly Gly Ile Gly Glu Ala Ile Val Asp Ile Pro Glu
                        130                 135                 140

Ile Pro Gly Phe Lys Asp Leu Glu Pro Met Glu Gln Phe Ile Ala Gln
            145                 150                 155                 160

Val Asp Leu Cys Val Asp Cys Thr Thr Gly Cys Leu Lys Gly Leu Ala
                            165                 170                 175

Asn Val Lys Cys Ser Asp Leu Leu Lys Lys Trp Leu Pro Ser Arg Cys
                            180                 185                 190

Ala Thr Phe Ala Ser Lys Ile Gln Ala Gln Val Asp Lys Ile Lys Gly
                            195                 200                 205

Ala Gly Gly Ser
                210
```

<210> SEQ ID NO 20
<211> LENGTH: 212
<212> TYPE: PRT
<213> ORGANISM: Artificial Sequence
<220> FEATURE:
<223> OTHER INFORMATION: ALuc22

<400> SEQUENCE: 20

```
            Met Met Gly Val Lys Leu Ile Phe Ala Val Leu Cys Val Ala Val Ala
            1               5                   10                  15

Gln Ala Asn Ala Thr Ile Asn Glu Asn Phe Glu Asp Ile Asp Leu Val
                            20                  25                  30

Ala Ile Gly Gly Ser Phe Ala Asp Leu Glu Thr Asp Leu Phe Thr Ile
                        35                  40                  45

Val Glu Asp Met Asn Val Ile Ser Arg Asp Thr Asp Val Asp Ala Asn
                50                  55                  60

Arg Gly Gly Arg Gly Arg Gly Lys Leu Pro Gly Lys Lys Leu Pro
            65                  70                  75                  80

Leu Glu Val Leu Lys Glu Leu Glu Ala Asn Ala Gln Lys Ala Gly Cys
                            85                  90                  95

Thr Arg Gly Cys Leu Ile Cys Leu Ser His Ile Lys Cys Thr Ala Lys
                            100                 105                 110

Met Lys Lys Trp Leu Pro Gly Arg Cys Glu Ser Trp Glu Gly Asp Lys
                            115                 120                 125

Glu Thr Gly Gln Gly Gly Ile Gly Glu Ala Ile Val Asp Ile Pro Glu
                        130                 135                 140

Ile Pro Gly Phe Lys Asp Leu Glu Pro Met Glu Gln Phe Ile Ala Gln
```

-continued

```
              145                 150                 155                 160
Val Asp Leu Cys Val Asp Cys Thr Thr Gly Cys Leu Lys Gly Leu Ala
                    165                 170                 175

Asn Val Lys Cys Ser Asp Leu Leu Lys Lys Trp Leu Pro Ser Arg Cys
                180                 185                 190

Ala Thr Phe Ala Ser Lys Ile Gln Ala Gln Val Asp Lys Ile Lys Gly
                195                 200                 205

Ala Gly Gly Ser
            210

<210> SEQ ID NO 21
<211> LENGTH: 212
<212> TYPE: PRT
<213> ORGANISM: Artificial Sequence
<220> FEATURE:
<223> OTHER INFORMATION: ALuc23

<400> SEQUENCE: 21

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Val Asp Ala Asn
        50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                    165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
            210

<210> SEQ ID NO 22
<211> LENGTH: 212
<212> TYPE: PRT
<213> ORGANISM: Artificial Sequence
<220> FEATURE:
<223> OTHER INFORMATION: ALuc24

<400> SEQUENCE: 22

Met Met Gly Ile Lys Val Leu Phe Ala Leu Ile Cys Phe Ala Leu Val
1               5                   10                  15
```

```
Gln Ala Asn Pro Thr Glu Asn Lys Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Asn Met Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190

Lys Gly Phe Ala Asn Lys Ile Gln Ala Glu Val Asp Thr Ile Lys Gly
                195                 200                 205

Leu Gly Gly Ser
            210

<210> SEQ ID NO 23
<211> LENGTH: 212
<212> TYPE: PRT
<213> ORGANISM: Artificial Sequence
<220> FEATURE:
<223> OTHER INFORMATION: ALuc25

<400> SEQUENCE: 23

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
 50                  55                  60

Arg Gly Gly Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160
```

```
Val Asp Leu Cys Ala Asp Cys Thr Thr Gly Cys Leu Lys Gly Leu Ala
            165                 170                 175

Asn Val Lys Cys Ser Ala Leu Leu Lys Lys Trp Leu Pro Ser Arg Cys
        180                 185                 190

Ala Gly Phe Ala Asp Lys Ile Gln Ala Gln Val Asp Thr Ile Lys Gly
    195                 200                 205

Ala Gly Gly Ser
    210

<210> SEQ ID NO 24
<211> LENGTH: 212
<212> TYPE: PRT
<213> ORGANISM: Artificial Sequence
<220> FEATURE:
<223> OTHER INFORMATION: ALuc26

<400> SEQUENCE: 24

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
50                  55                  60

Arg Gly Gly Arg Gly Arg Gly Lys Leu Pro Gly Lys Lys Leu Pro
65              70                  75                  80

Leu Glu Val Leu Lys Glu Leu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asn Leu Ala Pro Met Glu Gln Phe Ile Ala Gln
145                 150                 155                 160

Val Asp Leu Cys Ala Asp Cys Thr Thr Gly Cys Leu Lys Gly Leu Ala
            165                 170                 175

Asn Val Lys Cys Ser Asn Leu Leu Lys Lys Trp Leu Pro Ser Arg Cys
        180                 185                 190

Ala Gly Phe Ala Asn Lys Ile Gln Ala Gln Val Asp Thr Ile Lys Gly
    195                 200                 205

Leu Gly Gly Ser
    210

<210> SEQ ID NO 25
<211> LENGTH: 212
<212> TYPE: PRT
<213> ORGANISM: Artificial Sequence
<220> FEATURE:
<223> OTHER INFORMATION: ALuc27

<400> SEQUENCE: 25

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30
```

```
Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Gly Gly Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Phe Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Phe Cys Ser Phe Leu Leu Lys Lys Trp Leu Pro Ser Arg Cys
            180                 185                 190

Ala Gly Phe Ala Phe Lys Ile Gln Ala Gln Val Asp Thr Ile Lys Gly
            195                 200                 205

Leu Gly Gly Ser
 210

<210> SEQ ID NO 26
<211> LENGTH: 212
<212> TYPE: PRT
<213> ORGANISM: Artificial Sequence
<220> FEATURE:
<223> OTHER INFORMATION: ALuc28

<400> SEQUENCE: 26

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Gly Gly Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Tyr Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175
```

```
Asn Val Tyr Cys Ser Tyr Leu Leu Lys Lys Trp Leu Pro Ser Arg Cys
            180                 185                 190

Ala Gly Phe Ala Tyr Lys Ile Gln Ala Gln Val Asp Thr Ile Lys Gly
        195                 200                 205

Leu Gly Gly Ser
    210

<210> SEQ ID NO 27
<211> LENGTH: 212
<212> TYPE: PRT
<213> ORGANISM: Artificial Sequence
<220> FEATURE:
<223> OTHER INFORMATION: ALuc29

<400> SEQUENCE: 27

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Trp Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Trp Cys Ser Trp Leu Leu Lys Lys Trp Leu Pro Ser Arg Cys
            180                 185                 190

Ala Gly Phe Ala Trp Lys Ile Gln Ala Gln Val Asp Thr Ile Lys Gly
        195                 200                 205

Leu Gly Gly Ser
    210

<210> SEQ ID NO 28
<211> LENGTH: 212
<212> TYPE: PRT
<213> ORGANISM: Artificial Sequence
<220> FEATURE:
<223> OTHER INFORMATION: ALuc30

<400> SEQUENCE: 28

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
```

```
                35                  40                  45
Val Glu Asp Met Asn Val Ile Ser Arg Asp Thr Asp Val Asp Ala Asn
 50                  55                  60
Arg Ala Asp Arg Gly Arg Gly Lys Leu Pro Gly Lys Lys Leu Pro
 65                  70                  75                  80
Leu Glu Val Leu Lys Glu Leu Glu Ala Asn Ala Gln Lys Ala Gly Cys
                 85                  90                  95
Thr Arg Gly Cys Leu Ile Cys Leu Ser His Ile Lys Cys Thr Ala Lys
                100                 105                 110
Met Lys Lys Trp Leu Pro Gly Arg Cys Glu Ser Trp Glu Gly Asp Lys
                115                 120                 125
Glu Thr Gly Gln Gly Gly Ile Gly Glu Ala Ile Val Asp Ile Pro Glu
                130                 135                 140
Ile Pro Gly Phe Lys Glu Leu Ala Pro Met Glu Gln Phe Ile Ala Gln
145                 150                 155                 160
Val Asp Leu Cys Ala Asp Cys Thr Thr Gly Cys Leu Lys Gly Leu Ala
                165                 170                 175
Asn Val Lys Cys Ser Ala Leu Leu Lys Lys Trp Leu Pro Ser Arg Cys
                180                 185                 190
Ala Gly Phe Ala Asp Lys Ile Gln Ala Gln Val Asp Thr Ile Lys Gly
                195                 200                 205
Ala Gly Gly Ser
                210

<210> SEQ ID NO 29
<211> LENGTH: 212
<212> TYPE: PRT
<213> ORGANISM: Artificial Sequence
<220> FEATURE:
<223> OTHER INFORMATION: ALuc31

<400> SEQUENCE: 29

Met Met Gly Ile Lys Val Leu Phe Ala Leu Ile Cys Phe Ala Leu Val
  1               5                  10                  15
Gln Ala Asn His His His His His His His Asp Ile Val Gly Val
                 20                  25                  30
Glu Gly Lys Phe Gly Thr Thr Asp Leu Glu Thr Asp Leu Phe Thr Ile
                 35                  40                  45
Val Glu Asp Met Asn Val Ile Ser Arg Asp Thr Asp Val Asp Ala Asn
 50                  55                  60
Arg Ala Asp Arg Gly Arg Gly Glu Leu Pro Gly Lys Lys Leu Pro
 65                  70                  75                  80
Leu Glu Val Leu Lys Glu Leu Glu Ala Asn Ala Gln Lys Ala Gly Cys
                 85                  90                  95
Thr Arg Gly Cys Leu Ile Cys Leu Ser His Ile Lys Cys Thr Ala Lys
                100                 105                 110
Met Lys Lys Trp Leu Pro Gly Arg Cys Glu Ser Trp Glu Gly Asp Lys
                115                 120                 125
Glu Thr Gly Gln Gly Gly Ile Gly Glu Ala Ile Val Asp Ile Pro Glu
                130                 135                 140
Ile Pro Gly Phe Lys Glu Leu Ala Pro Met Glu Gln Phe Ile Ala Gln
145                 150                 155                 160
Val Asp Leu Cys Ala Asp Cys Thr Thr Gly Cys Leu Lys Gly Leu Ala
                165                 170                 175
Asn Val Lys Cys Ser Ala Leu Leu Lys Lys Trp Leu Pro Ser Arg Cys
```

```
                180                 185                 190
Ala Gly Phe Ala Asp Lys Ile Gln Ala Gln Val Asp Thr Ile Lys Gly
        195                 200                 205

Ala Gly Gly Ser
    210

<210> SEQ ID NO 30
<211> LENGTH: 212
<212> TYPE: PRT
<213> ORGANISM: Artificial Sequence
<220> FEATURE:
<223> OTHER INFORMATION: ALuc32

<400> SEQUENCE: 30

Met Met Gly Ile Lys Val Leu Phe Ala Leu Ile Cys Phe Ala Leu Val
1               5                   10                  15

Gln Ala Asn Glu Gln Lys Leu Ile Ser Glu Glu Asp Leu Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
50                  55                  60

Arg Ala Asp Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 31
<211> LENGTH: 212
<212> TYPE: PRT
<213> ORGANISM: Artificial Sequence
<220> FEATURE:
<223> OTHER INFORMATION: ALuc33

<400> SEQUENCE: 31

Met Met Gly Ile Lys Val Leu Phe Ala Leu Ile Cys Phe Ala Leu Val
1               5                   10                  15

Gln Ala Asn Met Met Tyr Pro Tyr Asp Val Pro Asp Tyr Ala Gly Val
            20                  25                  30

Glu Gly Lys Phe Gly Thr Thr Asp Leu Glu Thr Asp Leu Phe Thr Ile
        35                  40                  45
```

```
Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
210

<210> SEQ ID NO 32
<211> LENGTH: 212
<212> TYPE: PRT
<213> ORGANISM: Artificial Sequence
<220> FEATURE:
<223> OTHER INFORMATION: ALuc34

<400> SEQUENCE: 32

Met Met Gly Ile Lys Val Leu Phe Ala Leu Ile Cys Phe Ala Leu Val
 1               5                  10                  15

Gln Ala Asn Met Met Asp Tyr Lys Asp Asp Asp Lys Val Gly Val
                 20                  25                  30

Glu Gly Lys Phe Gly Thr Thr Asp Leu Glu Thr Asp Leu Phe Thr Ile
                 35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190
```

```
Ala Gly Phe Ala Asp Lys Ile Gln Ala Gln Val Asp Thr Ile Lys Gly
            195                 200                 205

Ala Gly Gly Ser
    210

<210> SEQ ID NO 33
<211> LENGTH: 194
<212> TYPE: PRT
<213> ORGANISM: Artificial Sequence
<220> FEATURE:
<223> OTHER INFORMATION: ALuc41

<400> SEQUENCE: 33

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Thr Ile Lys Gly Leu Ala
            180                 185                 190

Gly Ser

<210> SEQ ID NO 34
<211> LENGTH: 213
<212> TYPE: PRT
<213> ORGANISM: Artificial Sequence
<220> FEATURE:
<223> OTHER INFORMATION: ALuc42

<400> SEQUENCE: 34

Met Met Gly Ile Lys Val Leu Phe Ala Leu Val Cys Leu Ala Leu Val
1               5                   10                  15

Gln Ala Asn His His His His His His Asp Ile Val Asp Val
            20                  25                  30

Val Gly Asn Phe Trp Ala Ile Gly Val Asp Asn Asp Arg Asp Phe Thr
            35                  40                  45

Ile Ser Glu Asp Met Asn Val Ile Ser Arg Asp Thr Asp Val Asp Ala
50                  55                  60

Asn Arg Ala Asp Arg Ala Asp Arg Gly Lys Leu Pro Gly Lys Lys Leu
65                  70                  75                  80
```

```
Pro Lys Glu Val Leu Ile Glu Ile Glu Ala Asn Ala Lys Lys Ala Gly
                 85                  90                  95

Cys Thr Arg Gly Cys Leu Ile Cys Leu Ser Lys Ile Lys Cys Thr Ala
            100                 105                 110

Lys Met Lys Lys Trp Leu Pro Gly Arg Cys His Ser Tyr Glu Gly Asp
            115                 120                 125

Lys Asp Thr Gly Gln Gly Gly Ile Gly Glu Pro Ile Val Asp Ala Pro
            130                 135                 140

Glu Ile Pro Gly Phe Lys Asp Leu Thr Pro Met Glu Gln Phe Ile Ala
145                 150                 155                 160

Gln Val Asp Leu Cys Ala Asp Cys Thr Thr Gly Cys Leu Lys Gly Leu
                165                 170                 175

Ala Asn Val Lys Cys Ser Ala Leu Leu Lys Lys Trp Leu Pro Asp Arg
            180                 185                 190

Cys Ala Ser Phe Ala Asp Lys Ile Gln Lys Glu Val Asp Thr Ile Lys
            195                 200                 205

Gly Leu Ala Gly Ser
        210

<210> SEQ ID NO 35
<211> LENGTH: 194
<212> TYPE: PRT
<213> ORGANISM: Artificial Sequence
<220> FEATURE:
<223> OTHER INFORMATION: ALuc43

<400> SEQUENCE: 35

Met Met Gly Ile Lys Val Leu Phe Ala Leu Val Cys Leu Ala Leu Val
1               5                   10                  15

Gln Ala Lys Pro Thr Glu Asp Glu Asp Glu Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
            130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Thr Glu Val Asp Thr Ile Lys Gly Leu Ala
            180                 185                 190

Gly Ser

<210> SEQ ID NO 36
<211> LENGTH: 194
<212> TYPE: PRT
```

```
<213> ORGANISM: Artificial Sequence
<220> FEATURE:
<223> OTHER INFORMATION: ALuc44

<400> SEQUENCE: 36

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Gln Asp Thr Ile Lys Gly Leu Ala
            180                 185                 190

Gly Ser

<210> SEQ ID NO 37
<211> LENGTH: 194
<212> TYPE: PRT
<213> ORGANISM: Artificial Sequence
<220> FEATURE:
<223> OTHER INFORMATION: ALuc45

<400> SEQUENCE: 37

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
```

```
               130                 135                 140
Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Asn Ile Lys Gly Leu Ala
                180                 185                 190

Gly Ser

<210> SEQ ID NO 38
<211> LENGTH: 194
<212> TYPE: PRT
<213> ORGANISM: Artificial Sequence
<220> FEATURE:
<223> OTHER INFORMATION: ALuc46

<400> SEQUENCE: 38

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
                20                  25                  30

Val Gly Asn Phe Trp Ala Ile Gly Val Asp Asn Asp Arg Asp Phe Thr
                35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
                100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Ser Glu Val Ala Thr Ile Lys Gly Leu Ala
                180                 185                 190

Gly Ser

<210> SEQ ID NO 39
<211> LENGTH: 194
<212> TYPE: PRT
<213> ORGANISM: Artificial Sequence
<220> FEATURE:
<223> OTHER INFORMATION: ALuc47

<400> SEQUENCE: 39

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
                20                  25                  30

Val Gly Asn Phe Trp Ala Ile Gly Val Asp Asn Asp Arg Asp Phe Thr
                35                  40                  45
```

```
Ile Ser Ala Asp Arg Gly Lys Leu Pro Gly Lys Lys Leu Pro Lys Glu
         50                  55                  60

Val Leu Ile Glu Ile Glu Ala Asn Ala Lys Lys Ala Gly Cys Thr Arg
 65                  70                  75                  80

Gly Cys Leu Ile Cys Leu Ser Lys Ile Lys Cys Thr Ala Lys Met Lys
                 85                  90                  95

Lys Trp Leu Pro Gly Arg Cys His Ser Tyr Glu Gly Asp Lys Asp Thr
                100                 105                 110

Gly Gln Gly Gly Ile Gly Glu Pro Ile Val Asp Ala Pro Glu Ile Pro
                115                 120                 125

Gly Phe Lys Asp Leu Thr Pro Met Glu Gln Phe Ile Ala Gln Val Asp
                130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Gly Thr Ile Lys Gly Leu Leu
                180                 185                 190

Gly Ser

<210> SEQ ID NO 40
<211> LENGTH: 215
<212> TYPE: PRT
<213> ORGANISM: Artificial Sequence
<220> FEATURE:
<223> OTHER INFORMATION: ALuc48

<400> SEQUENCE: 40

Met Met Gly Ile Lys Val Leu Phe Ala Leu Ile Cys Phe Ala Leu Val
 1                   5                  10                  15

Gln Ala Asn Pro Thr Glu Asn Lys Asp Asp Ile Asp Ile Val Gly Val
                 20                  25                  30

Glu Gly Lys Phe Gly Thr Thr Asp Leu Glu Thr Asp Leu Phe Thr Ile
                 35                  40                  45

Val Glu Asp Met Asn Val Ile Ser Arg Asp Thr Asp Val Asp Ala Asn
 50                  55                  60

Arg Ala Asp Arg Gly Arg Arg Gly His Gly Gly Leu Pro Gly Lys Lys
 65                  70                  75                  80

Met Pro Leu Glu Val Leu Leu Glu Leu Glu Ala Asn Ala Gln Arg Ala
                 85                  90                  95

Gly Cys Thr Arg Gly Cys Leu Ile Cys Leu Ser Lys Ile Lys Cys Thr
                100                 105                 110

Ala Lys Met Lys Lys Trp Leu Pro Gly Arg Cys Glu Ser Trp Ala Gly
                115                 120                 125

Asp Lys Glu Thr Gly Gln Gly Gly Ile Thr Glu Glu Thr Val Asp
                130                 135                 140

Ile Pro Glu Ile Pro Gly Phe Lys Asp Leu Glu Pro Met Glu Gln Phe
145                 150                 155                 160

Ile Ala Gln Val Asp Leu Cys Val Asp Cys Thr Thr Gly Cys Leu Lys
                165                 170                 175

Gly Leu Ala Asn Val Lys Cys Ser Asp Leu Leu Lys Lys Trp Leu Pro
                180                 185                 190

Ser Arg Cys Ala Thr Phe Ala Ser Lys Ile Gln Ala Gln Val Asp Lys
                195                 200                 205
```

```
Ile Lys Gly Ala Gly Gly Ser
    210             215
```

<210> SEQ ID NO 41
<211> LENGTH: 194
<212> TYPE: PRT
<213> ORGANISM: Artificial Sequence
<220> FEATURE:
<223> OTHER INFORMATION: ALuc49

<400> SEQUENCE: 41

```
Met Met Gly Ile Lys Val Leu Phe Ala Leu Val Cys Leu Ala Leu Val
1               5                   10                  15

Gln Ala Lys Pro Thr Glu Asp Glu Asp Glu Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
                100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Tyr Ile Lys Gly Leu Ala
            180                 185                 190

Gly Ser
```

<210> SEQ ID NO 42
<211> LENGTH: 194
<212> TYPE: PRT
<213> ORGANISM: Artificial Sequence
<220> FEATURE:
<223> OTHER INFORMATION: ALuc50

<400> SEQUENCE: 42

```
Met Met Gly Ile Lys Val Leu Phe Ala Leu Val Cys Leu Ala Leu Val
1               5                   10                  15

Gln Ala Lys Pro Thr Glu Asp Glu Asp Glu Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95
```

```
Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Phe Ile Lys Gly Leu Ala
            180                 185                 190

Gly Ser
```

<210> SEQ ID NO 43
<211> LENGTH: 194
<212> TYPE: PRT
<213> ORGANISM: Artificial Sequence
<220> FEATURE:
<223> OTHER INFORMATION: ALuc51

<400> SEQUENCE: 43

```
Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Trp Ile Lys Gly Leu Ala
            180                 185                 190

Gly Ser
```

<210> SEQ ID NO 44
<211> LENGTH: 212
<212> TYPE: PRT
<213> ORGANISM: Artificial Sequence
<220> FEATURE:
<223> OTHER INFORMATION: ALuc52

<400> SEQUENCE: 44

```
Met Met Gly Ile Lys Val Leu Phe Ala Leu Ile Cys Phe Ala Leu Val
```

```
                1               5                   10                  15
            Gln Ala Asn His His His His His His His Asp Ile Val Gly Val
                            20                  25                  30

Glu Gly Lys Phe Gly Thr Thr Asp Leu Glu Thr Asp Leu Phe Thr Ile
                            35                  40                  45

Val Glu Asp Met Asn Val Ile Ser Arg Asp Thr Asp Val Asp Ala Asn
                        50                  55                  60

Arg Ala Asp Arg Gly Arg Arg Gly Lys Leu Pro Gly Lys Lys Leu Pro
            65                  70                  75                  80

Leu Glu Val Leu Lys Glu Leu Glu Ala Asn Ala Gln Lys Ala Gly Cys
                                85                  90                  95

Thr Arg Gly Cys Leu Ile Cys Leu Ser His Asp Trp Cys Thr Ala Lys
                            100                 105                 110

Met Lys Lys Trp Leu Pro Gly Arg Cys Glu Ser Trp Glu Gly Asp Lys
                        115                 120                 125

Glu Thr Gly Gln Gly Gly Ile Gly Glu Ala Val Val Asp Ile Leu Glu
                    130                 135                 140

Ile Pro Gly Phe Lys Glu Leu Ala Pro Met Glu Gln Phe Ile Ala Gln
            145                 150                 155                 160

Val Asp Leu Cys Ala Asp Cys Thr Thr Gly Cys Leu Lys Gly Leu Ala
                            165                 170                 175

Asn Val Lys Cys Ser Ala Leu Leu Lys Lys Trp Leu Pro Ser Arg Cys
                        180                 185                 190

Ala Gly Phe Ala Asp Lys Ile Gln Ala Gln Val Asp Thr Ile Lys Gly
                    195                 200                 205

Ala Gly Gly Ser
                    210

<210> SEQ ID NO 45
<211> LENGTH: 212
<212> TYPE: PRT
<213> ORGANISM: Artificial Sequence
<220> FEATURE:
<223> OTHER INFORMATION: ALuc53

<400> SEQUENCE: 45

Met Met Gly Ile Lys Val Leu Phe Ala Leu Ile Cys Phe Ala Leu Val
            1               5                   10                  15

Gln Ala Asn His His His His His His His Asp Ile Val Gly Val
                            20                  25                  30

Glu Gly Lys Phe Gly Asn Thr Asp Leu Glu Thr Asp Leu Phe Thr Ile
                            35                  40                  45

Val Glu Asp Met Asn Val Ile Ser Arg Asp Thr Asp Val Asp Ala Asn
                        50                  55                  60

Arg Ala Asp Arg Gly Arg Arg Gly Lys Leu Pro Gly Lys Lys Leu Pro
            65                  70                  75                  80

Leu Glu Val Leu Lys Glu Leu Glu Ala Asn Ala Gln Lys Ala Gly Cys
                                85                  90                  95

Thr Arg Gly Cys Leu Ile Cys Leu Ser His Asp Trp Cys Thr Ala Lys
                            100                 105                 110

Met Lys Lys Trp Leu Pro Gly Arg Cys Glu Ser Trp Glu Gly Asp Lys
                        115                 120                 125

Glu Thr Gly Gln Gly Gly Ile Gly Glu Ala Val Val Asp Ile Pro Glu
                    130                 135                 140

Ile Pro Gly Phe Lys Glu Leu Ala Pro Met Glu Gln Phe Ile Ala Gln
```

145                 150                 155                 160
Val Asp Leu Cys Ala Asp Cys Thr Thr Gly Cys Leu Lys Gly Leu Ala
                        165                 170                 175

Asn Val Lys Cys Ser Ala Leu Leu Lys Lys Trp Leu Pro Ser Arg Cys
                    180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 46
<211> LENGTH: 212
<212> TYPE: PRT
<213> ORGANISM: Artificial Sequence
<220> FEATURE:
<223> OTHER INFORMATION: ALuc55

<400> SEQUENCE: 46

Met Met Gly Ile Lys Val Leu Phe Ala Leu Ile Cys Phe Ala Leu Val
1               5                   10                  15

Gln Ala Asn His His His His His His His Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                    100                 105                 110

Met Lys Lys Trp Leu Pro Gly Arg Cys Glu Ser Trp Glu Gly Asp Glu
                115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                        165                 170                 175

Asn Leu Lys Cys Ser Ala Leu Leu Lys Lys Trp Leu Pro Ser Arg Cys
                    180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 47
<211> LENGTH: 212
<212> TYPE: PRT
<213> ORGANISM: Artificial Sequence
<220> FEATURE:
<223> OTHER INFORMATION: ALuc56

<400> SEQUENCE: 47

Met Met Gly Ile Lys Val Leu Phe Ala Leu Ile Cys Phe Ala Leu Val
1               5                   10                  15

-continued

Gln Ala Asn His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Gly Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Leu Leu Leu Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
        210

<210> SEQ ID NO 48
<211> LENGTH: 212
<212> TYPE: PRT
<213> ORGANISM: Artificial Sequence
<220> FEATURE:
<223> OTHER INFORMATION: ALuc57

<400> SEQUENCE: 48

Met Met Gly Ile Lys Val Leu Phe Ala Leu Ile Cys Phe Ala Leu Val
1               5                   10                  15

Gln Ala Asn Tyr His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Val Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Gly Leu Ala Pro Met Glu Gln Phe Ile Ala Gln
145                 150                 155                 160

```
Val Asp Leu Cys Ala Asp Cys Thr Thr Gly Cys Trp Lys Gly Trp Ala
            165                 170                 175

Asn Leu Lys Cys Ser Ala Leu Leu Lys Lys Trp Leu Pro Ser Arg Cys
        180                 185                 190

Ala Gly Phe Ala Asp Lys Ile Gln Ala Gln Val Asp Thr Ile Lys Gly
    195                 200                 205

Ala Gly Gly Ser
    210
```

```
<210> SEQ ID NO 49
<211> LENGTH: 69
<212> TYPE: PRT
<213> ORGANISM: Artificial Sequence
<220> FEATURE:
<223> OTHER INFORMATION: ALuc common partial sequence

<400> SEQUENCE: 49

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly
65
```

```
<210> SEQ ID NO 50
<211> LENGTH: 149
<212> TYPE: PRT
<213> ORGANISM: Artificial Sequence
<220> FEATURE:
<223> OTHER INFORMATION: ALuc common partial sequence

<400> SEQUENCE: 50

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
            85                  90                  95

Thr Arg Gly Cys Leu Ile Cys Leu Ser His Ile Lys Cys Thr Ala Lys
        100                 105                 110

Met Lys Lys Trp Leu Pro Gly Arg Cys Glu Ser Trp Glu Gly Asp Lys
    115                 120                 125

Glu Thr Gly Gln Gly Gly Ile Gly Glu Ala Ile Val Asp Ile Pro Glu
        130                 135                 140

Ile Pro Gly Phe Lys
145
```

```
<210> SEQ ID NO 51
```

<211> LENGTH: 122
<212> TYPE: PRT
<213> ORGANISM: Artificial Sequence
<220> FEATURE:
<223> OTHER INFORMATION: picALuc30

<400> SEQUENCE: 51

Lys Leu Pro Gly Lys Lys Leu Pro Leu Glu Val Leu Lys Glu Leu Glu
1               5                   10                  15

Ala Asn Ala Gln Lys Ala Gly Cys Thr Arg Gly Cys Leu Ile Cys Leu
            20                  25                  30

Ser His Ile Lys Cys Thr Ala Lys Met Lys Lys Trp Leu Pro Gly Arg
        35                  40                  45

Cys Glu Ser Trp Glu Gly Asp Lys Glu Thr Gly Gln Gly Gly Ile Gly
    50                  55                  60

Glu Ala Ile Val Asp Ile Pro Glu Ile Pro Gly Phe Lys Glu Leu Ala
65                  70                  75                  80

Pro Met Glu Gln Phe Ile Ala Gln Val Asp Leu Cys Ala Asp Cys Thr
                85                  90                  95

Thr Gly Cys Leu Lys Gly Leu Ala Asn Val Lys Cys Ser Ala Leu Leu
            100                 105                 110

Lys Lys Trp Leu Pro Ser Arg Cys Ala Gly
        115                 120

<210> SEQ ID NO 52
<211> LENGTH: 122
<212> TYPE: PRT
<213> ORGANISM: Artificial Sequence
<220> FEATURE:
<223> OTHER INFORMATION: picALuc16

<400> SEQUENCE: 52

Lys Leu Pro Gly Lys Lys Leu Pro Leu Glu Val Leu Lys Glu Leu Glu
1               5                   10                  15

Ala Asn Ala Gln Lys Ala Gly Cys Thr Arg Gly Cys Leu Ile Cys Leu
            20                  25                  30

Ser His Ile Lys Cys Thr Ala Lys Met Lys Lys Trp Leu Pro Gly Arg
        35                  40                  45

Cys Glu Ser Trp Glu Gly Asp Lys Glu Thr Gly Gln Gly Gly Ile Gly
    50                  55                  60

Glu Ala Ile Val Asp Ile Pro Glu Ile Pro Gly Phe Lys Asp Leu Glu
65                  70                  75                  80

Pro Met Glu Gln Phe Ile Ala Gln Val Asp Leu Cys Val Asp Cys Thr
                85                  90                  95

Thr Gly Cys Leu Lys Gly Leu Ala Asn Val Lys Cys Ser Asp Leu Leu
            100                 105                 110

Lys Lys Trp Leu Pro Ser Arg Cys Ala Thr
        115                 120

<210> SEQ ID NO 53
<211> LENGTH: 125
<212> TYPE: PRT
<213> ORGANISM: Artificial Sequence
<220> FEATURE:
<223> OTHER INFORMATION: picALuc48

<400> SEQUENCE: 53

His Gly Gly Leu Pro Gly Lys Lys Met Pro Leu Glu Val Leu Leu Glu
1               5                   10                  15

```
Leu Glu Ala Asn Ala Gln Arg Ala Gly Cys Thr Arg Gly Cys Leu Ile
            20                  25                  30

Cys Leu Ser Lys Ile Lys Cys Thr Ala Lys Met Lys Lys Trp Leu Pro
        35                  40                  45

Gly Arg Cys Glu Ser Trp Ala Gly Asp Lys Glu Thr Gly Gln Gly Gly
50                  55                  60

Ile Thr Glu Glu Thr Val Asp Ile Pro Glu Ile Pro Gly Phe Lys
65                  70                  75                  80

Asp Leu Glu Pro Met Glu Gln Phe Ile Ala Gln Val Asp Leu Cys Val
                85                  90                  95

Asp Cys Thr Thr Gly Cys Leu Lys Gly Leu Ala Asn Val Lys Cys Ser
            100                 105                 110

Asp Leu Leu Lys Lys Trp Leu Pro Ser Arg Cys Ala Thr
        115                 120                 125

<210> SEQ ID NO 54
<211> LENGTH: 140
<212> TYPE: PRT
<213> ORGANISM: Artificial Sequence
<220> FEATURE:
<223> OTHER INFORMATION: ALuc30_del_loop2N1

<400> SEQUENCE: 54

Arg Gly Arg Gly Lys Leu Pro Gly Lys Lys Leu Pro Leu Glu Val
1               5                   10                  15

Leu Lys Glu Leu Glu Ala Asn Ala Gln Lys Ala Gly Cys Thr Arg Gly
            20                  25                  30

Cys Leu Ile Cys Leu Ser His Ile Lys Cys Thr Ala Lys Met Lys Lys
        35                  40                  45

Trp Leu Pro Gly Arg Cys Glu Ser Trp Glu Gly Asp Lys Glu Thr Gly
    50                  55                  60

Gln Gly Gly Ile Gly Glu Ala Ile Val Gly Ser Phe Lys Glu Leu Ala
65                  70                  75                  80

Pro Met Glu Gln Phe Ile Ala Gln Val Asp Leu Cys Ala Asp Cys Thr
                85                  90                  95

Thr Gly Cys Leu Lys Gly Leu Ala Asn Val Lys Cys Ser Ala Leu Leu
            100                 105                 110

Lys Lys Trp Leu Pro Ser Arg Cys Ala Gly Phe Ala Asp Lys Ile Gln
        115                 120                 125

Ala Gln Val Asp Thr Ile Lys Gly Ala Gly Ser
    130                 135                 140

<210> SEQ ID NO 55
<211> LENGTH: 140
<212> TYPE: PRT
<213> ORGANISM: Artificial Sequence
<220> FEATURE:
<223> OTHER INFORMATION: ALuc16_del_loop2N1

<400> SEQUENCE: 55

Arg Gly Arg Gly Lys Leu Pro Gly Lys Lys Leu Pro Leu Glu Val
1               5                   10                  15

Leu Lys Glu Leu Glu Ala Asn Ala Gln Lys Ala Gly Cys Thr Arg Gly
            20                  25                  30

Cys Leu Ile Cys Leu Ser His Ile Lys Cys Thr Ala Lys Met Lys Lys
        35                  40                  45

Trp Leu Pro Gly Arg Cys Glu Ser Trp Glu Gly Asp Lys Glu Thr Gly
    50                  55                  60
```

```
Gln Gly Gly Ile Gly Glu Ala Ile Val Gly Ser Phe Lys Asp Leu Glu
 65                  70                  75                  80

Pro Met Glu Gln Phe Ile Ala Gln Val Asp Leu Cys Val Asp Cys Thr
                 85                  90                  95

Thr Gly Cys Leu Lys Gly Leu Ala Asn Val Lys Cys Ser Asp Leu Leu
            100                 105                 110

Lys Lys Trp Leu Pro Ser Arg Cys Ala Thr Phe Ala Ser Lys Ile Gln
        115                 120                 125

Ala Gln Val Asp Lys Ile Lys Gly Ala Gly Gly Ser
    130                 135                 140
```

<210> SEQ ID NO 56
<211> LENGTH: 143
<212> TYPE: PRT
<213> ORGANISM: Artificial Sequence
<220> FEATURE:
<223> OTHER INFORMATION: ALuc48_del_loop2N1

<400> SEQUENCE: 56

```
Arg Gly Arg Arg Gly His Gly Gly Leu Pro Gly Lys Lys Met Pro Leu
 1               5                  10                  15

Glu Val Leu Leu Glu Leu Glu Ala Asn Ala Gln Arg Ala Gly Cys Thr
                 20                  25                  30

Arg Gly Cys Leu Ile Cys Leu Ser Lys Ile Lys Cys Thr Ala Lys Met
            35                  40                  45

Lys Lys Trp Leu Pro Gly Arg Cys Glu Ser Trp Ala Gly Asp Lys Glu
        50                  55                  60

Thr Gly Gln Gly Gly Ile Thr Glu Glu Thr Val Gly Ser Phe Lys
 65                  70                  75                  80

Asp Leu Glu Pro Met Glu Gln Phe Ile Ala Gln Val Asp Leu Cys Val
                 85                  90                  95

Asp Cys Thr Thr Gly Cys Leu Lys Gly Leu Ala Asn Val Lys Cys Ser
            100                 105                 110

Asp Leu Leu Lys Lys Trp Leu Pro Ser Arg Cys Ala Thr Phe Ala Ser
        115                 120                 125

Lys Ile Gln Ala Gln Val Asp Lys Ile Lys Gly Ala Gly Gly Ser
    130                 135                 140
```

<210> SEQ ID NO 57
<211> LENGTH: 123
<212> TYPE: PRT
<213> ORGANISM: Artificial Sequence
<220> FEATURE:
<223> OTHER INFORMATION: Met_picALuc30

<400> SEQUENCE: 57

```
Met Lys Leu Pro Gly Lys Lys Leu Pro Leu Glu Val Leu Lys Glu Leu
 1               5                  10                  15

Glu Ala Asn Ala Gln Lys Ala Gly Cys Thr Arg Gly Cys Leu Ile Cys
                 20                  25                  30

Leu Ser His Ile Lys Cys Thr Ala Lys Met Lys Lys Trp Leu Pro Gly
            35                  40                  45

Arg Cys Glu Ser Trp Glu Gly Asp Lys Glu Thr Gly Gln Gly Gly Ile
        50                  55                  60

Gly Glu Ala Ile Val Asp Ile Pro Glu Ile Pro Gly Phe Lys Glu Leu
 65                  70                  75                  80

Ala Pro Met Glu Gln Phe Ile Ala Gln Val Asp Leu Cys Ala Asp Cys
```

```
                    85                  90                  95
Thr Thr Gly Cys Leu Lys Gly Leu Ala Asn Val Lys Cys Ser Ala Leu
                100                 105                 110

Leu Lys Lys Trp Leu Pro Ser Arg Cys Ala Gly
        115                 120
```

<210> SEQ ID NO 58
<211> LENGTH: 123
<212> TYPE: PRT
<213> ORGANISM: Artificial Sequence
<220> FEATURE:
<223> OTHER INFORMATION: Met_picALuc16

<400> SEQUENCE: 58

```
Met Lys Leu Pro Gly Lys Lys Leu Pro Leu Glu Val Leu Lys Glu Leu
1               5                   10                  15

Glu Ala Asn Ala Gln Lys Ala Gly Cys Thr Arg Gly Cys Leu Ile Cys
                20                  25                  30

Leu Ser His Ile Lys Cys Thr Ala Lys Met Lys Lys Trp Leu Pro Gly
            35                  40                  45

Arg Cys Glu Ser Trp Glu Gly Asp Lys Glu Thr Gly Gln Gly Gly Ile
50                  55                  60

Gly Glu Ala Ile Val Asp Ile Pro Glu Ile Pro Gly Phe Lys Asp Leu
65                  70                  75                  80

Glu Pro Met Glu Gln Phe Ile Ala Gln Val Asp Leu Cys Val Asp Cys
                85                  90                  95

Thr Thr Gly Cys Leu Lys Gly Leu Ala Asn Val Lys Cys Ser Asp Leu
                100                 105                 110

Leu Lys Lys Trp Leu Pro Ser Arg Cys Ala Thr
        115                 120
```

<210> SEQ ID NO 59
<211> LENGTH: 126
<212> TYPE: PRT
<213> ORGANISM: Artificial Sequence
<220> FEATURE:
<223> OTHER INFORMATION: Met_picALuc48

<400> SEQUENCE: 59

```
Met His Gly Gly Leu Pro Gly Lys Lys Met Pro Leu Glu Val Leu Leu
1               5                   10                  15

Glu Leu Glu Ala Asn Ala Gln Arg Ala Gly Cys Thr Arg Gly Cys Leu
                20                  25                  30

Ile Cys Leu Ser Lys Ile Lys Cys Thr Ala Lys Met Lys Lys Trp Leu
            35                  40                  45

Pro Gly Arg Cys Glu Ser Trp Ala Gly Asp Lys Glu Thr Gly Gln Gly
        50                  55                  60

Gly Ile Thr Glu Glu Thr Val Asp Ile Pro Glu Ile Pro Gly Phe
65                  70                  75                  80

Lys Asp Leu Glu Pro Met Glu Gln Phe Ile Ala Gln Val Asp Leu Cys
                85                  90                  95

Val Asp Cys Thr Thr Gly Cys Leu Lys Gly Leu Ala Asn Val Lys Cys
                100                 105                 110

Ser Asp Leu Leu Lys Lys Trp Leu Pro Ser Arg Cys Ala Thr
        115                 120                 125
```

<210> SEQ ID NO 60
<211> LENGTH: 141

<212> TYPE: PRT
<213> ORGANISM: Artificial Sequence
<220> FEATURE:
<223> OTHER INFORMATION: Met_ALuc30_del_loop2N1

<400> SEQUENCE: 60

```
Met Arg Gly Arg Arg Gly Lys Leu Pro Gly Lys Lys Leu Pro Leu Glu
1               5                   10                  15

Val Leu Lys Glu Leu Glu Ala Asn Ala Gln Lys Ala Gly Cys Thr Arg
            20                  25                  30

Gly Cys Leu Ile Cys Leu Ser His Ile Lys Cys Thr Ala Lys Met Lys
        35                  40                  45

Lys Trp Leu Pro Gly Arg Cys Glu Ser Trp Gly Asp Lys Glu Thr
    50                  55                  60

Gly Gln Gly Gly Ile Gly Glu Ala Ile Val Gly Ser Phe Lys Glu Leu
65                  70                  75                  80

Ala Pro Met Glu Gln Phe Ile Ala Gln Val Asp Leu Cys Ala Asp Cys
                85                  90                  95

Thr Thr Gly Cys Leu Lys Gly Leu Ala Asn Val Lys Cys Ser Ala Leu
            100                 105                 110

Leu Lys Lys Trp Leu Pro Ser Arg Cys Ala Gly Phe Ala Asp Lys Ile
        115                 120                 125

Gln Ala Gln Val Asp Thr Ile Lys Gly Ala Gly Ser
    130                 135                 140
```

<210> SEQ ID NO 61
<211> LENGTH: 141
<212> TYPE: PRT
<213> ORGANISM: Artificial Sequence
<220> FEATURE:
<223> OTHER INFORMATION: Met_ALuc16_del_loop2N1

<400> SEQUENCE: 61

```
Met Arg Gly Arg Arg Gly Lys Leu Pro Gly Lys Lys Leu Pro Leu Glu
1               5                   10                  15

Val Leu Lys Glu Leu Glu Ala Asn Ala Gln Lys Ala Gly Cys Thr Arg
            20                  25                  30

Gly Cys Leu Ile Cys Leu Ser His Ile Lys Cys Thr Ala Lys Met Lys
        35                  40                  45

Lys Trp Leu Pro Gly Arg Cys Glu Ser Trp Gly Asp Lys Glu Thr
    50                  55                  60

Gly Gln Gly Gly Ile Gly Glu Ala Ile Val Gly Ser Phe Lys Asp Leu
65                  70                  75                  80

Glu Pro Met Glu Gln Phe Ile Ala Gln Val Asp Leu Cys Val Asp Cys
                85                  90                  95

Thr Thr Gly Cys Leu Lys Gly Leu Ala Asn Val Lys Cys Ser Asp Leu
            100                 105                 110

Leu Lys Lys Trp Leu Pro Ser Arg Cys Ala Thr Phe Ala Ser Lys Ile
        115                 120                 125

Gln Ala Gln Val Asp Lys Ile Lys Gly Ala Gly Gly Ser
    130                 135                 140
```

<210> SEQ ID NO 62
<211> LENGTH: 144
<212> TYPE: PRT
<213> ORGANISM: Artificial Sequence
<220> FEATURE:
<223> OTHER INFORMATION: Met_ALuc48_del_loop2N1

<400> SEQUENCE: 62

Met Arg Gly Arg Arg Gly His Gly Gly Leu Pro Gly Lys Lys Met Pro
1               5                   10                  15

Leu Glu Val Leu Leu Glu Leu Glu Ala Asn Ala Gln Arg Ala Gly Cys
            20                  25                  30

Thr Arg Gly Cys Leu Ile Cys Leu Ser Lys Ile Lys Cys Thr Ala Lys
        35                  40                  45

Met Lys Lys Trp Leu Pro Gly Arg Cys Glu Ser Trp Ala Gly Asp Lys
    50                  55                  60

Glu Thr Gly Gln Gly Gly Ile Thr Glu Glu Thr Val Gly Ser Phe
65              70                  75                  80

Lys Asp Leu Glu Pro Met Glu Gln Phe Ile Ala Gln Val Asp Leu Cys
                85                  90                  95

Val Asp Cys Thr Thr Gly Cys Leu Lys Gly Leu Ala Asn Val Lys Cys
                100                 105                 110

Ser Asp Leu Leu Lys Lys Trp Leu Pro Ser Arg Cys Ala Thr Phe Ala
            115                 120                 125

Ser Lys Ile Gln Ala Gln Val Asp Lys Ile Lys Gly Ala Gly Gly Ser
        130                 135                 140

<210> SEQ ID NO 63
<211> LENGTH: 11
<212> TYPE: PRT
<213> ORGANISM: Artificial Sequence
<220> FEATURE:
<223> OTHER INFORMATION: Membrane localization signal

<400> SEQUENCE: 63

Met Leu Cys Cys Met Arg Arg Thr Lys Gln Val
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Cytoplasmic localization signal

<400> SEQUENCE: 64

Gly Arg Lys Lys Arg Arg Gln Arg Arg Arg
1               5                   10

<210> SEQ ID NO 65
<211> LENGTH: 4
<212> TYPE: PRT
<213> ORGANISM: Artificial Sequence
<220> FEATURE:
<223> OTHER INFORMATION: Endoplasmic reticulum (ER) localization signal

<400> SEQUENCE: 65

Lys Asp Glu Leu
1

<210> SEQ ID NO 66
<211> LENGTH: 8
<212> TYPE: PRT
<213> ORGANISM: Artificial Sequence
<220> FEATURE:
<223> OTHER INFORMATION: Nuclear localization signal (NLS)

<400> SEQUENCE: 66

Asp Pro Lys Lys Lys Arg Lys Val

```
1               5
```

<210> SEQ ID NO 67
<211> LENGTH: 6
<212> TYPE: PRT
<213> ORGANISM: Artificial Sequence
<220> FEATURE:
<223> OTHER INFORMATION: His-Tag

<400> SEQUENCE: 67

```
His His His His His His
1               5
```

<210> SEQ ID NO 68
<211> LENGTH: 8
<212> TYPE: PRT
<213> ORGANISM: Artificial Sequence
<220> FEATURE:
<223> OTHER INFORMATION: FLAG-tag

<400> SEQUENCE: 68

```
Asp Tyr Lys Asp Asp Asp Asp Lys
1               5
```

<210> SEQ ID NO 69
<211> LENGTH: 10
<212> TYPE: PRT
<213> ORGANISM: Artificial Sequence
<220> FEATURE:
<223> OTHER INFORMATION: Myc-tag

<400> SEQUENCE: 69

```
Glu Gln Lys Leu Ile Ser Glu Glu Asp Leu
1               5                   10
```

<210> SEQ ID NO 70
<211> LENGTH: 9
<212> TYPE: PRT
<213> ORGANISM: Artificial Sequence
<220> FEATURE:
<223> OTHER INFORMATION: HA-tag

<400> SEQUENCE: 70

```
Tyr Pro Tyr Asp Val Pro Asp Tyr Ala
1               5
```

<210> SEQ ID NO 71
<211> LENGTH: 14
<212> TYPE: PRT
<213> ORGANISM: Artificial Sequence
<220> FEATURE:
<223> OTHER INFORMATION: V5-tag

<400> SEQUENCE: 71

```
Gly Lys Pro Ile Pro Asn Pro Leu Leu Gly Leu Asp Ser Thr
1               5                   10
```

<210> SEQ ID NO 72
<211> LENGTH: 11
<212> TYPE: PRT
<213> ORGANISM: Artificial Sequence
<220> FEATURE:
<223> OTHER INFORMATION: T7-tag

<400> SEQUENCE: 72

```
Met Ala Ser Met Thr Gly Gly Gln Gln Met Gly
1               5                   10
```

<210> SEQ ID NO 73
<211> LENGTH: 171
<212> TYPE: PRT
<213> ORGANISM: oplophorus gracilirostris

<400> SEQUENCE: 73

```
Ala Val Phe Thr Leu Glu Asp Phe Val Gly Asp Trp Arg Gln Thr Ala
1               5                   10                  15

Gly Tyr Asn Leu Asp Gln Val Leu Glu Gln Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 74
<211> LENGTH: 148
<212> TYPE: PRT
<213> ORGANISM: Metrisia longa

<400> SEQUENCE: 74

```
Met Glu Ala Glu Ala Glu Arg Gly Lys Leu Pro Gly Lys Lys Leu Pro
1               5                   10                  15

Leu Glu Val Leu Ile Glu Leu Glu Ala Asn Ala Arg Lys Ala Gly Cys
            20                  25                  30

Thr Arg Gly Cys Leu Ile Cys Leu Ser Lys Ile Lys Cys Thr Ala Lys
        35                  40                  45

Met Lys Lys Tyr Ile Pro Gly Arg Cys Ala Asp Tyr Gly Gly Asp Lys
    50                  55                  60

Lys Thr Gly Gln Ala Gly Ile Val Gly Ala Ile Val Asp Ile Pro Glu
65                  70                  75                  80

Ile Ser Gly Phe Lys Glu Met Glu Pro Met Glu Gln Phe Ile Ala Gln
                85                  90                  95

Val Asp Arg Cys Ala Asp Cys Thr Thr Gly Cys Leu Lys Gly Leu Ala
            100                 105                 110

Asn Val Lys Cys Ser Asp Leu Leu Lys Lys Trp Leu Pro Gly Arg Cys
        115                 120                 125

Ala Thr Phe Ala Asp Lys Ile Gln Ser Glu Val Asp Asn Ile Lys Gly
    130                 135                 140

Leu Ala Gly Asp
145
```

<210> SEQ ID NO 75
<211> LENGTH: 185
<212> TYPE: PRT
<213> ORGANISM: Gaussia princeps

<400> SEQUENCE: 75

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185

POLYPEPTIDE HAVING LUCIFERASE ACTIVITY

SEQUENCE LISTING

A sequence listing in electronic (ASCII text file) format is filed with this application and incorporated herein by reference. The name of the ASCII text file is "2021_2605A_sequence_listing.txt"; the file was created on Apr. 27, 2022; the size of the file is 97,963 bytes.

BACKGROUND OF THE INVENTION

Field of the Invention

The present invention relates to a polypeptide with luciferase activity.

Description of the Background Art

In the basic biology field, diagnostic techniques, and testing techniques, luciferases are used as a reporter protein for detecting a target protein. As a reporter protein, luciferases as well as fluorescent proteins, fluorescent dyes, quantum dot, peroxidase, and the like are widely used. Fluorescent proteins, fluorescent dyes, and quantum dot have high fluorescence intensity but require excitation light, so they have drawbacks including the following: (1) they are phototoxic to cells; (2) the excitation light spectrum overlaps the fluorescence spectrum and therefore the signal-background ratio tends to be low, rendering them unsuitable for trace detection; and (3) the detector needs to be equipped with a built-in excitation light irradiator and a built-in spectral filter. Luciferase does not require excitation light, and therefore it has none of the above-described drawbacks. Moreover, detection with luciferase is more suitable for trace detection than colorimetric methods which employ peroxidase and the like.

Luciferases that have been reported so far include wild-type firefly-derived luciferase (FLuc), NanoLuc, TurboLuc, luciferase derived from copepod (*Gaussia princeps*) (GLuc), luciferase derived from sea pansy (*Renilla reniformis*), and luciferase derived from copepod (*Metridia longa*) (MLuc). Japanese Patent Laying-Open No. 2014-100137 (PTL 1) and International Patent Laying-Open No. WO 2017/057752 (PTL 2) disclose an artificial luciferase (Aluc) engineered by selecting frequent amino acids from the amino acid sequence of a copepod-derived luciferase.

CITATION LIST

Patent Literature

PTL 1: Japanese Patent Laying-Open No. 2014-100137
PTL 2: International Patent Laying-Open No. WO 2017/057752

SUMMARY OF THE INVENTION

Technical Problem

When intracellular expression of a fusion protein composed of luciferase and target protein is attempted, and if the luciferase is large, the fusion protein may not be expressed in a normal fashion or steric hindrance may occur to inhibit normal functioning of the target protein. Moreover, according to some report, the emission value of large luciferases tends to be affected by low-molecular compounds, and therefore such enzymes are unsuitable for drug screening. In the case of intermolecular interaction analysis via Bioluminescence Resonance Energy Transfer (BRET), signal intensity is inversely proportional to the sixth power of the distance between the luciferase and the fluorescent protein, which means a smaller luciferase gives a stronger signal.

Thus, a small luciferase is useful for luciferase applications. An object of the present invention is to provide a novel luciferase with a small molecular weight.

Solution to Problem

The present invention relates to a polypeptide with luciferase activity according to (A) or (B):

(A) an amino acid sequence as set forth in SEQ ID NO: 1 with deletion of amino acid residues at positions 1 to 69 and 204 to 221; or (B) an amino acid sequence as set forth in SEQ ID NO: 1 with deletion of amino acid residues at positions 1 to 69 and deletion or substitution of at least one of amino acid residues at positions 146 to 156.

Advantageous Effects of Invention

According to the present invention, a luciferase with a small molecular weight is provided.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2 shows amino acid sequence identity between picALuc30 and picALuc16.

FIG. 3 shows amino acid sequence identity between picALuc30 and picALuc48.

FIG. 4 shows amino acid sequence identity between picALuc48 and picALuc16.

FIG. 5 is a graph showing the emission value of picALuc in Experiment 2. The error bars represent ±1 SD (n=3).

DESCRIPTION OF THE PREFERRED EMBODIMENTS

<Polypeptide>

Figure 1:
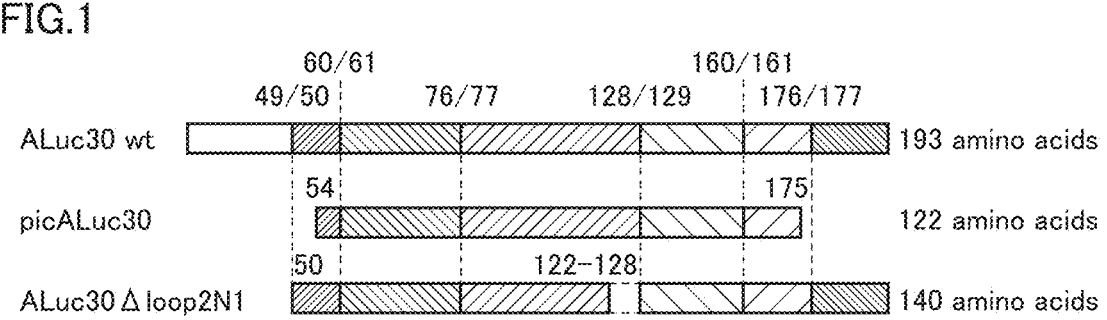
FIG. 1 shows the structure of an ALuc30 variant prepared in Examples.

The polypeptide according to the present invention has a luciferase activity. Luciferase refers to an enzyme that oxidizes luciferin and emits light during the oxidation. Luciferase activity herein refers to the activity of enzymatic reaction between a luciferase and a substrate, and it is measured by detecting light (emission spectrum) emitted when the substrate returns to the ground state after it was excited to the excited state due to the enzymatic reaction with the luciferase. The light emitted during the transition to the ground state can be detected with the use of a known luminometer (such as "GloMax" series manufactured by Promega, for example) or a known spectrophotometer (such as "Infinite 200 PRO" manufactured by TECAN, for example). By measuring the intensity every minute at a particular wavelength, the time course and the stability of emission can be detected. A shift of emission to a longer wavelength can be detected by performing measurement across the entire wavelength range.

The optimum pH and the optimum temperature for the luciferase activity may be the same as those for a known luciferase (such as a copepod-derived luciferase or an artificial luciferase, for example). Preferably, the luciferase activity is the same as the activity of a copepod-derived luciferase. The optimum pH for the luciferase activity is from 5.0 to 8.0, preferably 7.0, and the optimum temperature is from 4° C. to 30° C., preferably 25° C.

The luciferin is not particularly limited, and may be selected as appropriate for the particular luciferase. The luciferin may be a known substrate such as coelenterazine-based one, firefly-luciferin-based one, Cypridina-luciferin-based one, and/or furimazine, and it is preferably a coelenterazine-based substrate. Examples of the coelenterazine-based substrate include natural coelenterazine, coelenterazip ip, coelenterazine i, coelenterazine hcp, coelenterazine 400A, coelenterazine, coelenterazine cp, coelenterazine f, coelenterazine h, and coelenterazine n. The luciferin preferably includes coelenterazine or coelenterazine h.

An aspect of the polypeptide according to the present invention includes:

(A) an amino acid sequence as set forth in SEQ ID NO: 1 with deletion of amino acid residues at positions 1 to 69 and 204 to 221.

An aspect of the polypeptide according to the present invention includes:

(A1) amino acid residues at positions 75 to 203 of the amino acid sequence as set forth in SEQ ID NO: 1, and the number of amino acid residues may be 140 or less. The polypeptide according to the present invention may consist of amino acid residues at positions 75 to 203 of the amino acid sequence as set forth in SEQ ID NO: 1.

(A2) The polypeptide according to the present invention includes amino acid residues at positions 75 to 203 of the amino acid sequence as set forth in SEQ ID NO: 1, and the molecular weight of the polypeptide may be 20 kDa or less.

An aspect of the polypeptide according to the present invention includes:

(B) an amino acid sequence as set forth in SEQ ID NO: 1 with deletion of amino acid residues at positions 1 to 69 and deletion or substitution of at least one of amino acid residues at positions 146 to 156.

An aspect of the polypeptide according to the present invention may be:

(B1) an amino acid sequence that includes amino acid residues at positions 70 to 221 of the amino acid sequence as set forth in SEQ ID NO: 1 with deletion or substitution of at least one of amino acid residues at positions 146 to 156. The polypeptide according to the present invention may be a polypeptide consisting of amino acid residues at positions 70 to 221 of the amino acid sequence as set forth in SEQ ID NO: 1 with deletion or substitution of at least one of amino acid residues at positions 146 to 156.

The polypeptide according to the present invention may further comprise deletion of at least one of amino acid residues at positions 70 to 74, or deletion of all the amino acid residues at positions 70 to 74, of the amino acid sequence as set forth in SEQ ID NO: 1.

The polypeptide according to the present invention preferably includes deletion of 2 or more, 3 or more, 4 or more, 5 or more, 6 or more, or 7 or more of amino acid residues at positions 146 to 156 of the amino acid sequence as set forth in SEQ ID NO: 1. Into the deleted site, a linker sequence of one to several bases may be inserted. The polypeptide according to the present invention may have 6 or less, 5 or less, 4 or less, 3 or less, 2 or less, 1 or less, or 0 amino acid residues between positions 146 and 156 (inclusive) of the amino acid sequence as set forth in SEQ ID NO: 1.

The molecular weight of the polypeptide according to the present invention is preferably 20 kDa or less, more preferably 18 kDa or less, further preferably 15 kDa or less, further preferably 14 kDa or less, particularly preferably 13 kDa or less. The molecular weight of the polypeptide according to the present invention is 10 kDa or more, for example.

The number of amino acid residues of the polypeptide according to the present invention is, for example, 160 or less, preferably 155 or less, 150 or less, 146 or less, 143 or less, 140 or less, 136 or less, 133 or less, 130 or less, 126 or less, 123 or less, 122 or less, 121 or less, 120 or less, 119 or less, 118 or less, or 117 or less. The number of amino acid residues of the polypeptide according to the present invention is 100 or more, for example.

Among the amino acids represented by Xaa in SEQ ID NO: 1, amino acid residues at positions 3, 20-29, 31, 32, 35, 37, 64-66, 69, 76-77, 85-86, 89-90, 129, 140-144, 148-151, 159, 161, 188, 191, 202, and 206 are not particularly limited. Among these, amino acid residues at positions 22-23, 39-40, 76-77, 140, and 148-151 are optionally deleted. Preferably, amino acid residue at position 3 is E or G; amino acid residues at positions 20-29 form a PTENKDDI sequence (2 residues deleted, SEQ ID NO: 2), an ATINEEDI sequence (2 residues deleted, SEQ ID NO: 3), an ATINENFEDI sequence (SEQ ID NO: 4), an HHHHHHHH sequence (2 residues deleted, SEQ ID NO: 5), an EKLISEE sequence (2 residues deleted, SEQ ID NO: 6), an MMYPYDVP sequence (2 residues deleted, SEQ ID NO: 7), or an MMDYKDDD sequence (2 residues deleted, SEQ ID NO: 8); amino acid residue at position 31 is I, L, Y, or K; amino acid residue at position 32 is V or A; amino acid residue at position 35 is E or G; amino acid residue at position 37 is K or S; amino acid residues at positions 64-66 form an ANS sequence or a DAN sequence; amino acid residue at position 69 is D or G; amino acid residues at positions 76-77 form a GG sequence or are K (1 residue deleted) or optionally deleted; amino acid residues at positions 85-86 form an LE, KA, or KE sequence; amino acid residues at positions 89-90 form a KE sequence, an IE sequence, an LE sequence, or a KI sequence; amino acid residue at position 129 is E, G, or A; amino acid residues at positions 140-144 form a TEEET sequence (SEQ ID NO: 9), a GEAI sequence (1 residue deleted, SEQ ID NO: 10), or a VGAI sequence (1 residue deleted, SEQ ID NO: 11); amino acid residues at positions 148-151 form a GVLG sequence (SEQ ID NO: 12) or are I (3 residues deleted) or optionally deleted as a whole; amino acid residue at position 159 is D, E, N, F, Y, or W; amino acid residue at position 161 is E, A, or L; amino acid residue at position 188 is K, F, Y, or W; amino acid residue at position 191 is D, A, N, F, Y, or W; amino acid residue at position 202 is A or K; and amino acid residue at position 206 is S, D, N, F, Y, or W.

Amino acid residues at positions 13, 16, 174, and 218 of SEQ ID NO: 1 are hydrophobic amino acids (such as V, F, A, L, I, and G, for example), and preferably, amino acid residue at position 13 is V or F, amino acid residue at position 16 is V or A, amino acid residue at position 174 is V or A, and amino acid residue at position 218 is A or L.

Amino acid residues at positions 5, 67, 75, 101, 119, and 214 of SEQ ID NO: 1 are hydrophilic amino acids (such as Q, K, D, R, H, E, and T, for example), and preferably, amino acid residue at position 5 is Q or K, amino acid residue at position 67 is D or R, amino acid residue at position 75 is K, H, R, or E, amino acid residue at position 101 is T or H, amino acid residue at position 119 is K, E, or Q, and amino acid residue at position 211 is K or T.

Amino acid residues at positions 4, 6, 7, 10, 11, 15, 33, 34, 39-41, 63, 68, 74, 78, 83, 137, 160, and 203 of SEQ ID NO: 1 are aliphatic amino acids. Amino acid residues at positions 39, 40, and 70 are optionally deleted. Amino acid residues at positions 4, 6, 7, 10, 11, 15, 34, 63, 78, 83, and 160 are preferably high-molecular-weight aliphatic amino acids (such as I, V, L, and M, for example), and some of them (but not many of them) may be low-molecular-weight aliphatic amino acid(s). More preferably, amino acid residue at position 4 is I or V; amino acid residue at position 6 is V or L; amino acid residue at position 7 is L or I; amino acid residue at position 10 is L or V; amino acid residue at position 11 is I or L; amino acid residue at position 15 is L or V; amino acid residue at position 34 is I or V; amino acid residue at position 63 is L or V; amino acid residue at position 78 is L or M; amino acid residue at position 83 is L or M; and amino acid residue at position 160 is L or M. Amino acid residues at positions 33, 39-41, 68, 74, 137, and 203 are preferably low-molecular-weight aliphatic amino acids (such as A, G, and T, for example), and some of them (but not many of them) may be high-molecular-weight aliphatic amino acid(s). More preferably, amino acid residue at position 33 is G, L, or A; amino acid residue at position 39 is G or A or optionally deleted or S or F; amino acid residue at position 40 is T or optionally deleted; amino acid residue at position 41 is T or A; amino acid residue at position 68 is A or G; amino acid residue at position 74 is G or optionally deleted; amino acid residue at position 137 is G or A; and amino acid residue at position 203 is T or G.

Amino acid residues at positions 72, 73, 97, and 110 of SEQ ID NO: 1 are positively-charged amino acids (basic amino acids, such as K, R, and H). Amino acid residues at positions 72 and 73 are optionally deleted. Preferably, amino acid residues at positions 72 and 73 are R or optionally deleted, amino acid residue at position 97 is K or R, and amino acid residue at position 110 is H or K.

Amino acid residues at positions 62 and 211 of SEQ ID NO: 1 are negatively-charged amino acids (acidic amino acids, such as N, D, Q, and E), and preferably, amino acid residue at position 62 is N or D and amino acid residue at position 211 is Q or E.

Specific examples of the luciferase having the amino acid sequence as set forth in SEQ ID NO: 1 include ALuc10 (SEQ ID NO: 13), ALuc15 (SEQ ID NO: 14), ALuc16 (SEQ ID NO: 15), Aluc17 (SEQ ID NO: 16), Aluc18 (SEQ ID NO: 17), ALuc19 (SEQ ID NO: 18), ALuc21 (SEQ ID NO: 19), ALuc22 (SEQ ID NO: 20), ALuc23 (SEQ ID NO: 21), ALuc24 (SEQ ID NO: 22), ALuc25 (SEQ ID NO: 23), ALuc26 (SEQ ID NO: 24), ALuc27 (SEQ ID NO: 25), ALuc28 (SEQ ID NO: 26), ALuc29 (SEQ ID NO: 27), ALuc30 (SEQ ID NO: 28), ALuc31 (SEQ ID NO: 29), ALuc32 (SEQ ID NO: 30), ALuc33 (SEQ ID NO: 31), ALuc34 (SEQ ID NO: 32), ALuc41 (SEQ ID NO: 33), Aluc42 (SEQ ID NO: 34), ALuc43 (SEQ ID NO: 35), Aluc44 (SEQ ID NO: 36), ALuc45 (SEQ ID NO: 37), Aluc46 (SEQ ID NO: 38), ALuc47 (SEQ ID NO: 39), ALuc48 (SEQ ID NO: 40), ALuc49 (SEQ ID NO: 41), Aluc50 (SEQ ID NO: 42), ALuc51 (SEQ ID NO: 43), Aluc52 (SEQ ID NO: 44), ALuc53 (SEQ ID NO: 45), ALuc55 (SEQ ID NO: 46), Aluc56 (SEQ ID NO: 47), and ALuc57 (SEQ ID NO: 48). The luciferase having the amino acid sequence as set forth in SEQ ID NO: 1 may comprise deletion of some of or all of the amino acid residues at positions 1 to 19 (secretion signal), 20 to 31 (such as an antigen recognition site), and 217 to 221 (GS linker sequence).

A region from position 1 to position 71 of the amino acid sequence as set forth in SEQ ID NO: 1 may be an amino acid sequence as set forth in SEQ ID NO: 49. Typical examples of luciferase having this sequence include ALuc15, ALuc16, ALuc17, ALuc18, and ALuc24.

A region from position 1 to position 157 of the amino acid sequence as set forth in SEQ ID NO: 1 may be an amino acid sequence as set forth in SEQ ID NO: 50. Typical examples of luciferase having this sequence include ALuc22, ALuc25, ALuc26, ALuc27, ALuc28, and ALuc29.

By using the polypeptide according to the present invention, it is possible to decrease the size of luciferase. With the luciferase being small, when a fusion protein composed of the luciferase and a target protein or an antibody or the like is expressed within a cell, the fusion protein is likely to be expressed in a normal fashion and the target protein can be less likely to malfunction. With the luciferase being small, the emission value is less likely to be affected by low-molecular compounds, and therefore the luciferase can be suitably used as a reporter protein for drug or ligand screening. Also, in the case of intermolecular interaction analysis by bioluminescence resonance energy transfer (BRET), use of a small luciferase can give stronger detection signals. A small luciferase may be used for secretory luciferase. Secretory luciferase does not require cytolysis for emission value measurement, enabling measurement of time course of gene expression. A small luciferase is easily expressed within a cell, enabling expression and purification in a large quantity. A small luciferase can be expressed by various expression systems. Further, a small luciferase has excellent structural stability.

The polypeptide according to the present invention can have a high emission value. The emission peak value of the polypeptide according to the present invention is preferably the same as, or even higher than, that of a known luciferase such as NanoLuc and ALuc. A luciferase with a high emission value enables highly sensitive emission detection and makes it possible to lower the concentration limit for detection.

The polypeptide according to the present invention preferably has a high thermal stability; for example, at least 80% of the activity is preserved after heat treatment at a temperature of 50° C. for 10 minutes, and preferably at least 80% of the activity is preserved after heat treatment at a temperature of 60° C. for 10 minutes. A luciferase with a high thermal stability is less likely to become inactivated due to a temperature increase during transportation and the like, and is highly practical at the site of diagnosis, examination, and the like.

The enzyme activity of the polypeptide according to the present invention preferably exhibits an emission spectrum with a wide tail on the longer wavelength side, and its emission spectrum is shifted to the longer wavelength side as compared to, for example, a conventional copepod-derived luciferase. Because a longer wavelength transmits through a living body very well, a luciferase exhibiting an emission spectrum with a wide tail on the longer wavelength side is suitable for live imaging. When coelenterazine is used as a substrate, the polypeptide according to the present invention shows an emission wavelength peak preferably from 470 nm to 490 nm, more preferably at about 482 nm. When coelenterazine h is used as a substrate, the polypeptide according to the present invention shows an emission wavelength peak preferably from 470 nm to 490 nm, more preferably at about 488 nm.

The C terminus of ALuc has been considered as essential for binding to a substrate. A polypeptide according to an aspect of the present invention does not have the C terminus of ALuc but has luciferase activity. Therefore, it seems that the substrate-binding site of a polypeptide without the C terminus of ALuc has a structure different from that of ALuc.

The polypeptide according to the present invention may have an antibody recognition site in the middle or at the end of it. Examples of the antibody recognition site include, but not limited to, His-tag (HHHHHH) (SEQ ID NO: 67), FLAG-tag (DYKDDDDK) (SEQ ID NO: 68), Myc-tag (EQKLISEEDL) (SEQ ID NO: 69), and HA-tag (YPYDVPDYA) (SEQ ID NO: 70).

The polypeptide according to the present invention may have a functional peptide attached to its N terminus or C terminus. When a membrane localization signal (MLS) is attached to the N terminus or the C terminus, for example, the luciferase can be localized in the cell membrane. Herein, even when it is not clearly specified, when two or more peptides including a signal peptide are bonded to each other, a known linker may be used as appropriate to adjust the length, the reading frame, and the like. Having the luciferase localized in the cell membrane has some advantages: substrate and oxygen can be smoothly supplied from outside; and a luciferase-based luminescent probe (such as a luminescent capsule, for example), when used, can quickly respond to external signal.

The polypeptide according to the present invention preferably includes (a) an amino acid sequence as set forth in any one of SEQ ID NOs: 51 to 56, and may consist of an amino acid sequence as set forth in any one of SEQ ID NOs: 51 to 56. The amino acid sequence as set forth in SEQ ID NO: 51 is the amino acid sequence of artificial luciferase ALuc30 with deletion of the N terminus and the C terminus (picALuc30 in FIG. 1). The amino acid sequence as set forth in SEQ ID NO: 54 is the amino acid sequence of ALuc30 with deletion of the N terminal sequence and an intermediate sequence (ALuc30Δloop2N1 in FIG. 1). Similarly, the amino acid sequences as set forth in SEQ ID NOs: 52 and 53 are the amino acid sequences of artificial luciferases ALuc16 and ALuc48, respectively, with deletion of the N terminus and the C terminus. The amino acid sequences as set forth in SEQ ID NOs: 55 and 56 are the amino acid sequences of ALuc16 and ALuc48, respectively, with deletion of the N terminal sequence and an intermediate sequence.

The polypeptide according to the present invention preferably includes (b) an amino acid sequence having at least 85% identity to an amino acid sequence as set forth in any one of SEQ ID NOs: 51 to 56, and may consist of an amino acid sequence having at least 85% identity to an amino acid sequence as set forth in any one of SEQ ID NOs: 51 to 56. The polypeptide preferably has at least 90%, at least 95%, at least 96%, at least 97%, at least 98%, at least 99%, or at least 99.5% identity to an amino acid sequence as set forth in any one of SEQ ID NOs: 51 to 56.

The polypeptide according to the present invention preferably includes (c) an amino acid sequence as set forth in any one of SEQ ID NOs: 51 to 56 with deletion, substitution, insertion, or addition of one or several amino acid residues, and may consist of an amino acid sequence as set forth in any one of SEQ ID NOs: 51 to 56 with deletion, substitution, insertion, or addition of one or several amino acid residues. "Several" herein may be from 2 to 20, from 2 to 10, from 2 to 5, or from 2 to 3, for example.

The polypeptide according to the present invention may include an amino acid corresponding to a start codon (methionine in most cases) before amino acid residue at position 1. Amino acid sequences as set forth in SEQ ID NOs: 51 to 56 with methionine added to position 1 are shown as SEQ ID NOs: 57 to 62.

An aspect of the polypeptide according to the present invention may include the following (a1) to (c1), or may consist of the following (a1) to (c1):

(a1) an amino acid sequence as set forth in any one of SEQ ID NOs: 57 to 62;

(b1) an amino acid sequence having at least 85% identity to an amino acid sequence as set forth in any one of SEQ ID NOs: 57 to 62; or (c1) an amino acid sequence as set forth in any one of SEQ ID NOs: 57 to 62 with deletion, substitution, insertion, or addition of one or several amino acid residues.

The polypeptide preferably has at least 90%, at least 95%, at least 96%, at least 97%, at least 98%, at least 99%, or at least 99.5% identity to an amino acid sequence as set forth in any one of SEQ ID NOs: 57 to 62.

<Nucleic Acid Coding for Polypeptide>

A nucleic acid according to an embodiment of the present invention codes for the above-described polypeptide. From the nucleic acid coding for the above-described polypeptide, the above-described polypeptide can be produced. The nucleic acid is preferably DNA or RNA. The nucleic acid coding for the polypeptide may include a start codon on the 5' end side of the base sequence corresponding to the above-described polypeptide, and may include a stop codon at the 3' end of it. The nucleic acid may include an intron sequence. The nucleic acid according to an embodiment of the present invention can be obtained by chemical synthesis, PCR, or the like.

A nucleic acid according to an embodiment includes a nucleic acid that includes a base sequence in which a codon coding for an amino acid in a coding region is replaced by another codon coding for the same amino acid. From the viewpoint of enhancing expression of the polypeptide, the nucleic acid according to the present invention may be a nucleic acid that includes a base sequence in which codon usage has been changed so as to be suitable for the host living thing or for the type of the transformed cell.

<Vector>

A vector according to an embodiment of the present invention includes the above-described nucleic acid. The vector is a nucleic acid molecule capable of amplifying or retaining DNA, and examples thereof include expression vectors and cloning vectors. In an example, the above-described nucleic acid, which is inserted in an expression vector, is introduced into a host cell and/or the like, and expresses a polypeptide with luciferase activity. The expression vector may have a promoter sequence and a terminator sequence aimed at expressing a gene incorporated therein. The vector according to an embodiment of the present invention can be obtained by inserting the above-described nucleic acid into a suitable vector.

The vector may be, for example, a vector derived from a bacterial plasmid, a vector derived from a yeast plasmid, a viral vector, a cosmid vector, a phagemid vector, an artificial chromosome vector, and/or the like. Examples of the vector include pBR322, pUC plasmid vector, and pET-based plasmid vector. More specifically, when *Escherichia coli* is used as the host cell, pUC19, pUC18, pUC119, pBluescriptII, and/or pET32 may be used, for example. When a mammalian cell is used as the host cell, pRc/RSV, pRc/CMV, retroviral vector, adenoviral vector, adeno-associated virus vector, and/or the like may be used, for example.

<Transformed Cell>

A transformed cell according to an embodiment of the present invention is a cell that has the above-described nucleic acid introduced therein. The nucleic acid, when it is being introduced into the cell, may be contained in a vector. The transformed cell is capable of expressing the luciferase. The luciferase may be secreted into the supernatant. Examples of the method for introducing the nucleic acid into the cell include chemical techniques such as calcium phosphate method, DEAE-dextran method, and cationic liposome method; biological techniques such as adenoviral vector, vaccinia virus vector, retroviral vector, and HVJ liposome; and physical techniques such as electroporation, DNA direct injection, and gene gun. A suitable introduction method may be selected depending on the cell used for introduction.

The cell into which the nucleic acid is introduced may be either a eukaryotic cell or a prokaryotic cell, and examples include bacterial cells, fungal cells, plant cells, animal cells, and insect cells. The cell may be a yeast cell, an *Escherichia coli* cell, or a mammalian cell. The mammal includes human, cow, horse, sheep, monkey and ape, pig, mouse, rat, hamster, guinea pig, rabbit, and dog.

<Reporter Protein and Reporter Analysis Method>

The polypeptide according to the present invention may be used as a reporter protein to carry out reporter analysis. The polypeptide according to the present invention may replace a luminescent substance or a fluorescent substance in a reporter analysis method that uses a conventional luciferase or a variety of fluorescent proteins.

The reporter protein herein refers to a luminescent label used for investigating the behavior of a target protein, a target nucleic acid, or a target gene in a cell. The reporter analysis method herein refers to an analytic method that involves using the polypeptide according to the present invention as a reporter protein and observing a factor such as whether or not light is emitted or the amount, timing, or location of emission, which reflects the intracellular behavior of a target protein or a target gene elicited in response to external stimulation. More specifically, the reporter analysis method may be regarded as a method for qualitatively or quantitatively measuring the location, timing, or amount of expression of a target gene, in the form of the location, timing, or amount of emission of the reporter protein. In the reporter assay, multiple enzymes or proteins capable of emitting light of different wavelengths may be concurrently used.

The reporter analysis may be carried out in the living body of a mammal or the like, or in a cultured cell, or in a test tube. Under in vivo conditions such as in a living body, a reporter gene consisting of a nucleic acid coding for an amino acid sequence constituting the above-described polypeptide, for example, is coupled to a target gene and incorporated into a vector, which is then introduced into a target cell. Examples of the cultured cell include mammalian cells used in typical genetic recombination, such as COS cells, CHO-K1 cells, HeLa cells, HEK293 cells, and NIH3T3 cells; bacterial cells such as those of yeast and *Escherichia coli*; and insect cells.

Next, the reporter analysis method according to the present invention will be described, where it is classified into three types ("basic", "inducible", and "activatable") according to Niu et al., Theranostics, 2, 2012, 413. and also, the application of the polypeptide according to the present invention to each of these analytic methods is explained.

(1) Basic Method

The basic method is the simplest reporter analysis system, where a target protein to be investigated for its behavior is coupled to and labelled with luciferase. When the polypeptide according to the present invention is used as a reporter protein in the basic method, a fusion protein which includes the polypeptide according to the present invention and the target protein or a protein capable of binding the target protein may be prepared. This method is different from other reporter analysis methods, in that the fusion protein is expressed by means of a non-regulatory promoter.

The fusion protein may also be used for in vivo imaging of the target protein.

Typically, the fusion protein is prepared by fusing the reporter protein to the N terminus or the C terminus of the target protein, but it may also be prepared by dividing the reporter protein into the N terminal portion and the C terminal portion and fusing them to the target protein directly or via other peptide sequence(s).

The fusion protein encompasses the following: (i) a single-piece fusion protein that is expressed from a nucleic acid coding for a fusion protein including the polypeptide according to the present invention and the target protein or a protein (including a peptide) capable of recognizing the target protein; and (ii) a coupled fusion protein that is obtained by separately expressing the polypeptide according to the present invention and the target protein or a protein capable of recognizing the target protein and coupling them by chemical reaction. Examples of the technique to couple the separately-expressed proteins, etc. by chemical reaction include coupling via a crosslinker, coupling via avidin-biotin binding, and coupling via chemical reaction of amino acid residues.

Examples of the fusion protein include a luciferase-labelled antibody that is an antibody coupled to a luciferase. Regarding this fusion protein, the reporter gene may be coupled to the upstream or downstream of cDNA for a single-chain variable region fragment (scFv) of the antibody, for example, to prepare a chimeric DNA, and the resulting DNA may be inserted into a suitable expression vector, which may then be introduced into a cell for expression, and thereby the fusion protein may be obtained.

(2) Inducible Method

In the inducible method, unlike in the basic method, reporter expression is regulated by a promoter. Luciferase has been used as a reporter protein in the inducible method for analyzing the timing and amount of gene expression when preparing recombinant proteins by recombinant DNA technique, and especially, it has been widely used as an indicator of changes in the timing and amount of expression elicited in response to external stimulation. Examples of an analysis system included in the inducible method include reporter gene assay, yeast two-hybrid assay, mammal two-hybrid assay, bioluminescence resonance energy transfer (BRET), protein splicing assay (PSA), protein complementation assay (PCA), and circular permutation assay. When the polypeptide according to the present invention is used as a reporter gene in these analysis methods, the measuring performance of these assays can be dramatically enhanced.

(i) Reporter Gene Assay

A reporter gene assay method is generally used as a means for analyzing the activation of transcription factor as well as the regulation of gene expression elicited in response to external stimulation. For example, it is used for detecting an endocrine disruptor (an environmental hormone) that interferes with signal transduction intermediated by a nuclear receptor. Expression of a target gene associated with signal transduction intermediated by a nuclear receptor (such as a hormone response gene, for example) is triggered by bonding of a ligand-receptor complex to a cis region that is responsible for regulating transcription of the gene (a hormone response element). A plasmid that has a reporter gene incorporated to the downstream of the cis region of a variety of hormone response genes is introduced into a cell, and the amount of a hormone molecule or an endocrine disruptor that can be a ligand is detected in the form of emission value.

Use of firefly luciferase (which has been widely used) in a reporter gene assay method has the following disadvantages: [1] due to the high molecular weight, it takes long for the expression to occur, putting heavy burdens on the host cell; and [2] due to the low emission intensity, it usually takes one to two days following stimulation for a sufficient amount of luciferase (reporter) is accumulated; these disadvantages will be resolved by selecting the polypeptide according to the present invention as a reporter protein.

Use of the polypeptide according to the present invention as a reporter protein is advantageous in that, due to the very high emission intensity of the reporter, measurement can be performed in a very short time after stimulation. This enables a significant reduction of measurement time as compared to conventional reporter proteins, and also, this offers a high over-time stability of emission to enable emission measurement in a cell line that exhibits a poor gene transfer efficiency. In addition, the shifted emission to a longer wavelength offers a higher permeation through the cell membrane and/or the skin. Further, the decreased background offers a higher precision in measurement.

In order to apply the polypeptide according to the present invention to reporter gene assay, for example, the luciferase may be coupled to a known eukaryotic expression vector that has a special promoter mounted upstream, and the resulting vector may be introduced into a eukaryotic cell, followed by, after a lapse of a certain period of time, measurement of the emission value under conditions with or without signal (stimulation). As the expression vector for reporter gene assay capable of mounting the polypeptide according to the present invention thereon, a known pTransLucent vector may be used, and the mounting can be easily carried out by a known method.

(ii) Two-Hybrid Method

A two-hybrid method is a technique for investigating protein-to-protein interaction, and the firstly-established one was a yeast two-hybrid (Y2H) system, which was established in 1989 using yeast (*Saccharomyces cerevisiae*). By taking advantage of the fact that a GAL4 protein (a transcriptional activator) DNA-binding domain (GAL4 DBD) is separable from a transcriptional activation domain, it is possible to express GAL4 DBD and a certain protein A (bait) in the form of a fusion protein to see if it interacts with protein B (prey), which is expressed at the same time in the cell and made to form a fusion protein with a transcriptional activation domain (TA). When protein A binds to protein B, it means that DBD comes close to TA to allow the DNA-binding domain (DBD) to bind to base sequence "UASG", thereby facilitating the expression of the reporter gene downstream. When the reporter gene is a luciferase, bioluminescence can be monitored in the presence of a specific substrate to measure the affinity between protein A and protein B, enabling the screening for a protein or a peptide that is capable of interacting with protein A (bait). In this case, protein B (prey) may also be provided by means of expression library.

As the host cell, not only a yeast cell but also a bacterial cell such as *Escherichia coli*, a mammalian cell, and/or an insect cell may be used. In that case, not only GAL4 DBD (which is a yeast-derived transcriptional activator) but also "LexA", a repressor protein derived from *Escherichia coli*, may be used, for example. A DNA coding for them is coupled to a DNA coding for a bait protein (namely, the above certain protein A) such as a ligand-binding region of a ligand-response transcriptional regulator, and then coupled to the downstream of a promoter that is capable of functioning in the host cell. As "a transcriptional activation region of a transcriptional activator", GAL4 transcriptional activation region, B42 acidic transcriptional activation region derived from *Escherichia coli*, and/or transcriptional activation region of herpes simplex virus VP16 may be used, for example. A DNA coding for the transcriptional activation region is coupled to a DNA coding for a prey protein (namely, the above certain protein B), and then coupled to the downstream of a promoter that is capable of functioning in the host cell.

Examples of a vector that has a DNA coding for a DNA-binding region of transcriptional regulator GAL4 and is also usable in a budding yeast as a host cell include plasmid pGBT9 (manufactured by Clontech). Examples of a vector that has a DNA coding for GAL4 transcriptional activation region and is also usable in a budding yeast include plasmid pGAD424 (manufactured by Clontech). Examples of a vector that has a DNA coding for GAL4 DNA-binding region and is also usable in a mammalian cell include pM (manufactured by Clontech) and pBIND (manufactured by Promega), and examples of a vector that has a DNA coding for a transcriptional activation region of herpes simplex virus VP16 and is also usable in a mammalian cell include pVP16 (manufactured by Clontech) and pACT (manufactured by Promega). Further, examples of a vector that has a DNA coding for LexA DNA-binding region and is also usable in a mammalian cell include pLexA (manufactured by Clontech), and examples of a vector that has a DNA coding for B42 and is also usable in a mammalian cell include pB42AD (manufactured by Clontech).

For example, a vector that has the polypeptide according to the present invention inserted as a reporter gene to the downstream of a region such as GAL4-binding region ("UASG") may be constructed; when a mammalian host is used, commercially-available pG5Luc vector (Promega) and/or pFR-Luc vector (Stratagene) may be used and on which the polypeptide according to the present invention may be easily mounted by a known method to replace the firefly luciferase originally mounted on the vector. Replacing chloramphenicol acetyltransferase (CAT) of commercially-available pG5CAT vector (Clontech) may also be adopted.

(3) Activatable Method

The activatable method is a reporter analysis method that exploits the ability of reporter itself to actively respond to ligand stimulation to emit light. Typical examples include monomolecular bioluminescent probes and luminescent capsules, and other applicable assays include protein complementation assay (PCA) and protein splicing assay (PSA).

(i) Production of Luminescent Fusion Protein (Luminescent Capsule)

By binding a membrane localization signal (MLS) to the C terminus of the polypeptide according to the present invention, it is possible to localize luciferase itself in or at the cell membrane. This molecular design for luciferase localization in the cell membrane allows for smooth supply of substrate and oxygen, enabling stable visualization of bioluminescence with a very high luminance. In this procedure, a gene for any polypeptide and/or protein may be inserted, as a cargo, between the nucleic acid coding for luciferase itself and the nucleic acid coding for the signal peptide. This allows for efficient delivery of the cargo protein to the cell membrane surface, and also makes the delivered location emit light. As an example, a DEVD sequence and/or an IETD sequence (each of which responds to cell death) may be attached to where the protein is coupled, as a cargo, to create a system that can actively respond to and visualize cell death using caspase-3 and/or caspase-8 activity as a signal. A luminescent fusion protein having this structure is also called "luminescent capsule". A luminescent capsule may also be used for assessing toxicity of chemical substances.

As compared to a conventional luminescent probe, the luminescent capsule has advantages of having very high luminance and stable emission properties and responding even to an analyte that does not permeate through the cell membrane. The basic structure of the luminescent capsule is "a membrane localization signal (MLS)" attached to "the C terminus of the luciferase itself". Polypeptides according to the present invention may be tandemly linked for enhancing the emission amount of the enzyme. The luminescent capsule allows for visualization of the action of a compound that triggers a change of cell surface morphology such as cell death, as a change of cell membrane surface morphology, making the observation easier. Preferably, a polypeptide that triggers a change of cell membrane surface morphology, or its partial recognition sequence, or more specifically the full-length or partial recognition sequence of G-protein coupled receptor (GPCR), c-Src, and/or the like, may be inserted between the C terminus of the luciferase itself and MLS. By inserting a cell-death-inducing polypeptide or its recognition sequence between the C terminus of the luciferase itself and MLS as a cargo, cell death can be visualized. More specifically, by inserting, as a cargo, a peptide sequence (usually of 20 or less amino acid residues, preferably of 10 or less amino acid residues) recognized by various caspases and proteases (such as serine protease and cysteine protease) and digestive enzymes (such as trypsin and amylase), or an amino acid sequence including a DEVD sequence or an IETD sequence, cell death can be visualized by means of caspase-3 activity. Further, by linking a fluorescent protein or another luciferase between the luciferase itself and MLS as a cargo, the amount of emission on the cell membrane surface is increased, enabling easier observation of cell membrane morphology. Because the luminescent capsule also responds to a ligand that does not permeate through the cell membrane, it enables screening for a wide range of stimulators.

The luminescent capsule is a luminescent fusion protein in which any protein or polypeptide intended to be expressed on the cell membrane surface is inserted between the C terminus side of the polypeptide according to the present invention and a membrane localization signal (MLS), and typically, it may be either:

(a) a luminescent fusion protein in which a fluorescent protein or a luciferase (which may be an enzyme other than the polypeptide according to the present invention) is inserted between the C terminus side of the polypeptide according to the present invention and a membrane localization signal (MLS); or (b) a luminescent fusion protein in which a polypeptide that triggers a change of cell membrane morphology, or a polypeptide of 20 or less amino acid residues, preferably of 10 or less amino acid residues, that is recognized by the above polypeptide is inserted between the C terminus side of the polypeptide according to the present invention and a membrane localization signal (MLS). As the polypeptide that triggers a change of cell membrane morphology, a polypeptide capable of inducing cell death is preferable, and caspase and a polypeptide of 20 or less amino acid residues that includes its recognition sequence "DEVD" or "IETD" are particularly preferable.

(ii) Application to Luminescent Probe

By incorporating the polypeptide according to the present invention into a monomolecular luminescent probe or a bimolecular luminescent probe, it is possible to observe the presence or absence of a ligand and the intensity of the ligand activity, with a high luminance. The components of the probe may be coupled in such a manner that, [1] near luciferase that is divided into two parts (N terminus fragment and C terminus fragment), [2] a ligand-binding protein capable of responding to a target ligand and [3] a recognition protein capable of recognizing bonding of the ligand to the ligand-binding protein are coupled, and thereby a high-performance luminescent probe may be provided. When, in the luminescent probe, the recognition protein recognizes the bonding of the ligand to the ligand-binding protein, the two enzyme fragments can complement each other to change the activity of the enzyme. When this occurs, the high luminance and stability of this divided enzyme allows for an improved detection limit and a highly reliable measurement.

The monomolecular luminescent probe is a known bioluminescent probe characterized in that it has all of its visualization and imaging components in a single fusion molecule. In one example, the N terminus fragment and the C terminus fragment of the polypeptide according to the present invention are included within a fusion protein that includes a ligand-binding protein and a recognition protein of the ligand-binding protein as its essential components. The bimolecular luminescent probe refers to a type of bioluminescent probe in which the N terminus fragment and the C terminus fragment of the polypeptide according to the present invention are present, respectively, in a fusion protein including a ligand-binding protein and in a fusion protein including a recognition protein.

When the polypeptide according to the present invention is used in a bioluminescent probe, it needs to be divided into the N terminus fragment and the C terminus fragment, and it may be divided or cleaved at a position corresponding to position 125/126, 129/130, 133/134, 137/138, 141/142, or 146/147, of ALuc16.

The specific technique for using the polypeptide according to the present invention as a monomolecular luminescent probe follows a known technique. Specifically, the polypeptide according to the present invention is divided into two components, and a chimeric DNA is designed that codes for a luminescent probe in which a ligand-binding protein is linearly bonded to a peptide sequence capable of recognizing a conformational change elicited by ligand-protein bonding. Typically, the chimeric DNA is subcloned into a vector that is suitable for the cell to be used for expression, and then the vector is introduced into the cell, followed by expression in the cell; alternatively, a regulatory sequence may be coupled to the upstream of the chimeric DNA for direct introduction into the cell. As the target cell, a cell derived from a mammal such as humans is preferable, and it may be a cell present in a living body or it may be a cultured cell that retains its original cellular function. It may be yeast cells, insect cells, and/or prokaryotic cells such as *Escherichia coli*. The specific type of the vector is not particularly limited, and a vector that allows for expression in an expression host may be selected as appropriate. As the method for introduction into the cell, a known transfection method such as microinjection and/or electroporation may be used. Alternatively, a lipid-based cell introduction method (such as BioPORTER (Gene Therapy Systems) and/or Chariot (Active Motif)) may also be adopted.

Because a bioluminescent probe having the polypeptide according to the present invention is introduced in the form of a chimeric DNA into a cell and then expressed as a fusion protein in the cell, by stimulating the transformed cell with a ligand and then measuring any change in the amount of emission from the cell, it is possible to evaluate the characteristics of the ligand, the extent of activity, and the like.

In the case of forming the polypeptide according to the present invention within a bioluminescent probe, "the ligand-binding protein" eligible to be mounted together with the polypeptide may be a protein having a ligand-binding site capable of binding the ligand. The ligand-binding protein may, upon ligand bonding, undergo conformational change, or undergo phosphorylation, or facilitate protein-protein interaction, for example. As the ligand-binding protein of this type, a nuclear receptor (NR) whose ligand is a hormone, a chemical substance, or a signaling protein, a cytokine receptor, or a variety of protein kinases is used, for example. The ligand-binding protein is selected as appropriate depending on the target ligand. The ligand intended to bind to the ligand-binding protein is not particularly limited provided that it is capable of binding to the ligand-binding protein, and it may be an extracellular ligand that is taken from outside into inside the cell, or may be an intracellular ligand that is produced inside the cell upon extracellular stimulation. The extracellular ligand may be, for example, an agonist or an antagonist to a receptor protein (such as a nuclear receptor and/or a G protein-binding receptor, for example). It may also be a signaling protein such as a cytokine, a chemokine, or insulin, capable of specifically binding to a protein involved in intracellular signal transduction, an intracellular second messenger, a lipid second messenger, a phosphorylated amino acid residue, a G protein-binding receptor ligand, and/or the like.

When an intracellular second messenger, a lipid second messenger, and/or the like is targeted as the ligand, for example, the ligand-binding protein may be a binding domain of the second messenger. The "second messenger" is intended to mean an intracellular signal transduction substance that is newly produced in the cell upon bonding of an extracellular signal transduction substance such as a hormone and/or a neurotransmitter to a receptor present on the cell membrane. Examples of the second messenger include cGMP, AMP, PIP, PIP2, PIP3, inositol triphosphate (IP3), IP4, $Ca^{2+}$, diacylglycerol, and arachidonic achid. For example, for targeting $Ca^{2+}$ as a second messenger, calmodulin (CaM) may be used as the ligand-binding protein.

(iii) Bioluminescence Resonance Energy Transfer (BRET) Molecular Probe

The polypeptide according to the present invention may be used in any method intended to detect intermolecular interaction, such as ligand-protein interaction or protein-protein interaction, for example. A BRET molecular probe according to an embodiment comprises the polypeptide according to the present invention and a fluorescent substance. Energy transfer from a luminescence donor to a fluorescence receptor causes a shift in the distribution of emission spectrum. This energy transfer allows for in vitro or in vivo real-time monitoring of intermolecular interaction. As an example, a fusion protein of the polypeptide according to the present invention coupled to a target molecule (such as a target protein, a ligand, a nucleic acid, and/or a lipid), and a fusion protein of a molecule (a protein, a ligand, a nucleic acid, and/or a lipid) capable of binding to a target molecule coupled to a fluorescent substance are prepared. The polypeptide according to the present invention and the target molecule may be coupled to each other via a suitable linker (such as a peptide, a nucleic acid, a polymer, an ester bond, a PEG linker, and/or a carbon chain, for example). When the target molecule comes close to the molecule capable of binding to the target molecule, the polypeptide according to the present invention comes close to the fluorescent substance, and thereby a BRET signal is detected. An assay system that includes a BRET molecular probe may include luciferin. A molecule that competes against the bonding of the target molecule (such as a molecule capable of binding to the target molecule but not coupled to the fluorescent substance, for example) may be added to decrease the BRET signal. When the BRET signal is decreased, intermolecular interaction may be detected (competitive binding assay).

Usually, the absorption spectrum of the fluorescent substance overlaps the emission spectrum of the polypeptide according to the present invention. Usually, the wavelength peak of the luciferase is at a distance from the wavelength peak of the fluorescent substance, and the approximate distance may be 80 nm, 100 nm, 120 nm, or 140 nm, for example. The fluorescent substance may be a fluorescent protein, a fluorescent dye, or a chromophore. Examples of the fluorescent substance include xanthene derivatives (such as fluorescein, rhodamine, Oregon green, eosin, and Texas red, for example), cyanine derivatives (such as cyanine, indocarbocyanine, oxacarbocyanine, thiacarbocyanine, and merocyanine, for example), naphthalene derivatives (such as dansyl and Prodan derivatives, for example), oxadiazole derivatives (such as pyridyloxazole, nitrobenzoxadiazole, and benzoxadiazole, for example), pyrene derivatives (such as Cascade blue, for example), oxazine derivatives (such as Nile red, Nile blue, Cresyl violet, and Oxazine 170, for example), acridine derivatives (such as proflavine, Acridine orange, and Acridine yellow, for example), arylmethine derivatives (such as auramine, Crystal violet, and Malachite green, for example), tetrapyrrole derivatives (such as porphine, phthalocyanine, and bilirubin, for example), CF dye (Biotium), BODIPY (Invitrogen), ALEXA FLuoR (Invitrogen), DYLIGHT FLUOR (Thermo Scientific, Pierce), ATTO and TRACY (Sigma-Aldrich), FluoProbes (Interchim), DY and MEGASTOKES (Dyomics), SULFO CY dye (CYANDYE, LLC), SETAU and SQUARE DYES (SETA BioMedicals), QUASAR and CAL FLUOR dyes (Biosearch Technologies), SURELIGHT DYES (APC, RPE, PerCP, phycobilisome) (Columbia Biosciences), APC, APCXL, RPE, BPE (Phyco-Biotech), autofluorescent proteins (such as YFP, RFP, mCherry, and mKate, for example), and quantum dot nanocrystals. The fluorescent substance may be a rhodamine analog (such as carboxyrhodamine analogs, for example).

Other examples of the BRET molecular probe include a fusion protein of the polypeptide according to the present invention linked to a fluorescent substance via, as a linker, a protein that can be digested by a certain protease. In the absence of the certain protease, the luciferase comes close to the fluorescent substance, and thereby a BRET fluorescent signal is emitted. In the presence of the certain protease, the protein is digested to cause separation of the luciferase from the fluorescent substance, and thereby the light is quenched. This method allows for detection of the presence of the certain protease.

(iv) Protein Complementation Assay (PCA)

The polypeptide according to the present invention may be used in a method for detecting ligand-protein interaction or protein-protein interaction or the proximity between them, such as protein complementation assay (PCA) or enzyme fragmentation assay. PCA provides a means for detecting interaction between two biomolecules, such as between two polypeptides. For example, the polypeptide according to the present invention is divided into two fragments and they are fused, respectively, to molecules to be investigated proximity. When the target molecules interact with each other, the two polypeptide fragments interact with each other to form a complete luciferase, and thereby emission is detected.

(v) Intracellular Imaging

The gene coding for the polypeptide according to the present invention may be stably introduced into various cell lines. Intracellular imaging with the use of the luciferase may be carried out by a known method. As an example, the polypeptide may be stably introduced into an undifferentiated cell in an embryo, an ES cell, and/or an induced pluripotent stem (iPS) cell.

The polypeptide according to the present invention may be coupled to a suitable signal peptide, and thereby may be used for high-luminance imaging of cell organelles. For example, an "MLCCMRRTKQV sequence" (SEQ ID NO: 63) derived from GAP-43 may be added to the N terminus or the C terminus of the polypeptide to enable localization to the cell membrane. A "GRKKRRQRRR sequence" (SEQ ID NO: 64) may be added to enable localization to the cytoplasm. "KDEL" (SEQ ID NO: 65) may be added to enable localization to endoplasmic reticula (ER), and a "DPKKKRKV sequence" (SEQ ID NO: 66) may be added to enable localization to the cell nucleus. An antigen site such as HIS-tag (HHHHHH) (SEQ ID NO: 67), FLAG-tag (DYKDDDDK) (SEQ ID NO: 68), Myc-tag (EQKLISEEDL) (SEQ ID NO: 69), HA-tag (YPYDVPDYA) (SEQ ID NO: 70), V5-tag (GKPIPNPLLGLDST) (SEQ ID NO: 71), and/or T7-tag (MASMTGGQQMG) (SEQ ID NO: 72) may be attached to allow for application for immunostaining and separation/purification in cell-free systems. In this case, known techniques such as immunostaining and immunocytochemistry are applicable.

Other terms and concepts herein are specified in detail in the description of the embodiments of the invention and in Examples. Each term is basically from IUPAC-IUB Commission on Biochemical Nomenclature, or is based on the meaning of the term widely used in the field. Moreover, various techniques used for implementing the invention, except for the techniques that are specifically presented with their sources, can be easily and surely implemented by a person skilled in the art based on known documents and the like. For example, genetic engineering and molecular biology techniques may be implemented by methods described in, for example, J. Sambrook, E. F. Fritsch & T. Maniatis, "Molecular Cloning: A Laboratory Manual (2nd edition)", Cold Spring Harbor Laboratory Press, Cold Spring Harbor, New York (1989); D. M. Glover et al. ed., "DNA Cloning", 2nd ed., Vol. 1 to 4, (The Practical Approach Series), IRL Press, Oxford University Press (1995); Ausubel, F. M. et al., Current Protocols in Molecular Biology, John Wiley & Sons, New York, N. Y, 1995; Edited by The Japanese Biochemical Society, "Second Series Biochemistry Laboratory Course 1, Genetic Research Method II" (which is, in Japanese, "Zoku-Seikagaku Jikken Kouza 1, Idenshi Kenkyu-hou II"), Tokyo Kagaku Dozin (1986); Edited by The Japanese Biochemical Society, "New Biochemistry Laboratory Course 2, Nucleic Acid III (Recombinant DNA technique)" (which is, in Japanese, "Shin-Seikagaku Jikken Kouza 2, Kakusan III (Kumikae DNA Gijutu)"), Tokyo Kagaku Dozin (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); or methods described in

EXAMPLES

Next, a more detailed description will be given of the present invention referring to Examples, which are not intended to limit the scope of the present invention.

<Experiment 1: Preparation of picALuc Plasmid>

A luciferase that had an amino acid sequence corresponding to positions 20 to 221 of SEQ ID NO: 1 and also had an amino acid sequence of positions 20 to 212 of ALuc30 (SEQ ID NO: 28) (without a signal sequence) was defined as ALuc30 wt. The sequence of ALuc30 wt is shown in FIG. 1. The molecular weight of ALuc30 wt is about 21 kDa. ALuc consists of two helix structures, a loop structure, a helix structure, a (helix structure)-(loop structure)-(helix structure), two small helix structures, a helix structure, and a small helix structure, in this order from the N terminus. As shown in FIG. 1, picALuc30 (SEQ ID NO: 51) including amino acids at positions 54 to 175 of ALuc30 wt, without the N terminus and the C terminus of ALuc30 wt was prepared. picALuc30 was inserted into a pcDNA3.1(+) vector (Thermo Fisher Scientific). In the same manner, with the use of ALuc16 (SEQ ID NO: 15) and ALuc48 (SEQ ID NO: 40) instead of ALuc30, expression plasmids picALuc16 (SEQ ID NO: 52) and picALuc48 (SEQ ID NO: 53) each having an amino acid sequence corresponding to picALuc30 were prepared. picALuc30 had a size of 13 kDa. To the N terminus of each variant, His-tag was added, and to the C terminus, Flag-tag was added.

The amino acid sequences of picALuc30 and picALuc16 had 96% identity (FIG. 2); the amino acid sequences of picALuc30 and picALuc48 had 85% identity (FIG. 3); and the amino acid sequences of picALuc48 and picALuc16 had 90% identity (FIG. 4).

<Experiment 2: Measurement of Emission Value of picALuc>

(1) COS-7 cells derived from the kidney of African green monkey were inoculated in a 24-well dish, and on the next day, subconfluency was attained.

(2) 25 µL of Opti-MEM (Thermo Fisher Scientific), 400 ng (2 µL) of the plasmid, and 1 µL of P3000 (Invitrogen) were mixed.

(3) 25 µL of Opti-MEM and 1 µL of lipofectoamine 3000 (Invitrogen) were mixed.

(4) (2) and (3) were mixed together, followed by incubation at room temperature for 5 minutes.

(5) The mixture was added to the medium of (1).

(6) 500 µL of Dulbecco's modified Eagle's medium was added, followed by culturing the cells at 37° C. for 1 day and then collecting the medium. The medium contained secretion-expressed luciferase.

(7) To 100 µL of the luciferase-containing medium, coelenterazine was added as a substrate at a final concentration of 5 µM, followed by measuring the emission value by using Enspire multi-mode plate reader (PerkinElmer).

picALuc30 exhibited an emission value the same as or higher than that of ALuc30 wt (FIG. 5). For both picALuc16 and picALuc48, sufficiently high emission values were measured.

<Experiment 3: Preparation of Δloop Plasmid>

Figure 6:
FIG. 6 shows the conformation of picALuc30.

A putative conformation of picALuc30 is shown in FIG. 6. picALuc30 had a plurality of loop structures. Among these, the amino acid sequences for three loops (loop 1, loop 2, and loop 3) were deleted to prepare variants. Amino acid residues for loop 1 (position 96 to position 100 of ALuc30 wt), those for loop 2 (position 122 to position 128 of ALuc30 wt), or those for loop 3 (position 156 to position 161 of ALuc30 wt) were deleted from ALuc30 wt, and Gly-Ser was inserted. Further, the N terminus of ALuc30 wt (position 1 to position 49) was also deleted. Thus, expression plasmids ALuc30Δloop1N1, ALuc30Δloop2N1 (SEQ ID NO: 54), and ALuc30Δloop3N1, in each of which the N terminus and a loop were deleted, were prepared. ALuc30Δloop2N1 had a size of 14 kDa.

<Experiment 4: Measurement of Emission Value of ALucΔloop>

Figure 7:
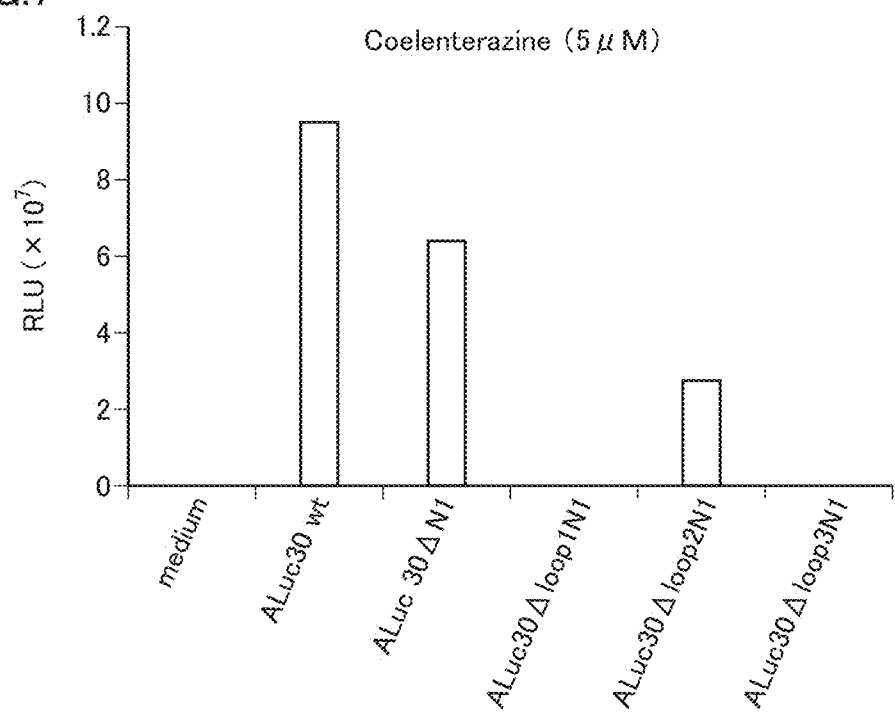
FIG. 7 is a graph showing the emission value of ΔloopN1 in Experiment 4.

By the same manner as in Experiment 2, the emission value was measured. ALuc30Δloop2N1 had about half the emission value of ALuc30ΔN1, which only lacked the N terminus as compared thereto (FIG. 7). The emission values of ALuc30Δloop1N1 and ALuc30Δloop3N1 were markedly low.

<Experiment 5: Comparison with Known Luciferase> picALuc prepared in Experiment 1 was compared with known NanoLuc, TurboLuc, and GLuc. NanoLuc is known to have a small size of about 19 kDa, a very high emission value, and a high thermal stability. TurboLuc is known to have a small size of about 16 kDa, a relatively high emission value, and a high thermal stability. GLuc is known to have a small size of 20 kDa, and when it is secretion expressed from cells, have a low emission value as compared to ALuc, and have a high thermal stability. For the preparation of NanoLuc, TurboLuc, and GLuc, plasmids having sequences as set forth in SEQ ID NO: 73, SEQ ID NO: 74, and SEQ ID NO: 75, respectively, inserted into a pcDNA3.1 vector were used.

Figure 8:
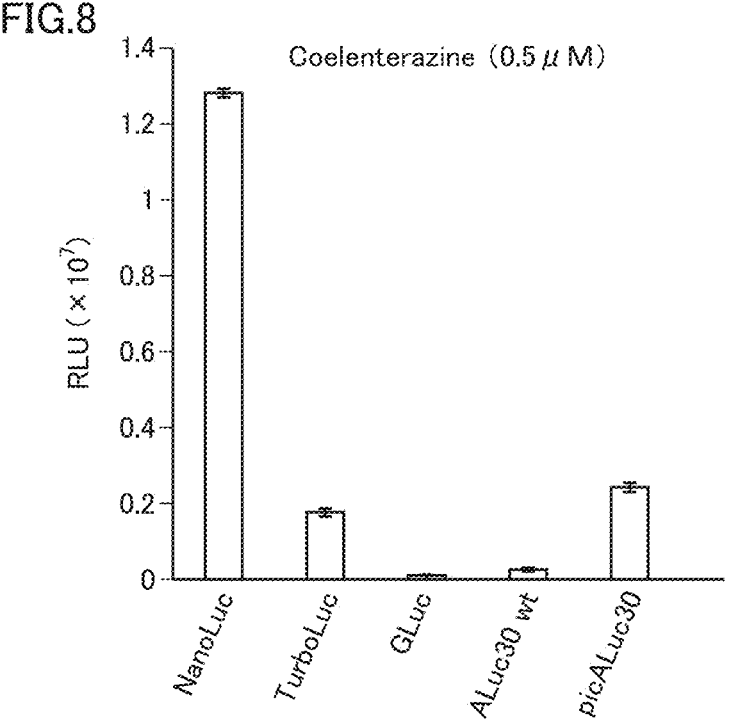
FIG. 8 is a graph of the emission value obtained when coelenterazine (0.5 μM) was added as a substrate to luciferase in Experiment 5. The error bars represent ±1 SD (n=3).
Figure 9:
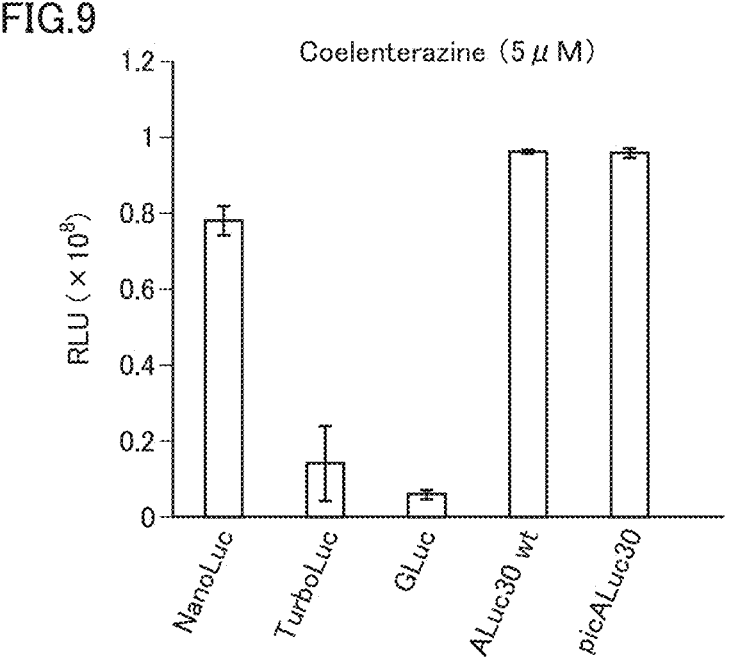
FIG. 9 is a graph of the emission value obtained when coelenterazine (5 μM) was added as a substrate to luciferase in Experiment 5. The error bars represent ±1 SD (n=3).

The emission value was measured in the same manner as in Experiment 2 except that the final concentration of coelenterazine was changed to 0.5 µM. The emission values were as follows: NanoLuc>>picALuc30>TurboLuc>ALuc30 wt>GLuc (FIG. 8). The emission value was measured in the same manner as in Experiment 2 except that the final concentration of coelenterazine was changed to 5 µM. The emission values were as follows: ALuc30 wt=picALuc30>NanoLuc>TurboLuc>GLuc (FIG. 9).

Figure 10:
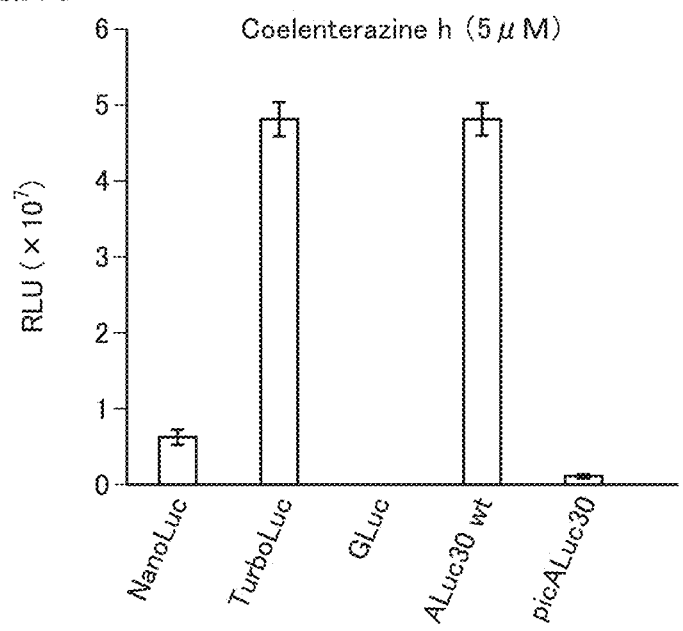
FIG. 10 is a graph of the emission value obtained when coelenterazine h (5 μM) was added as a substrate to luciferase in Experiment 5. The error bars represent ±1 SD (n=3).
Figure 11:
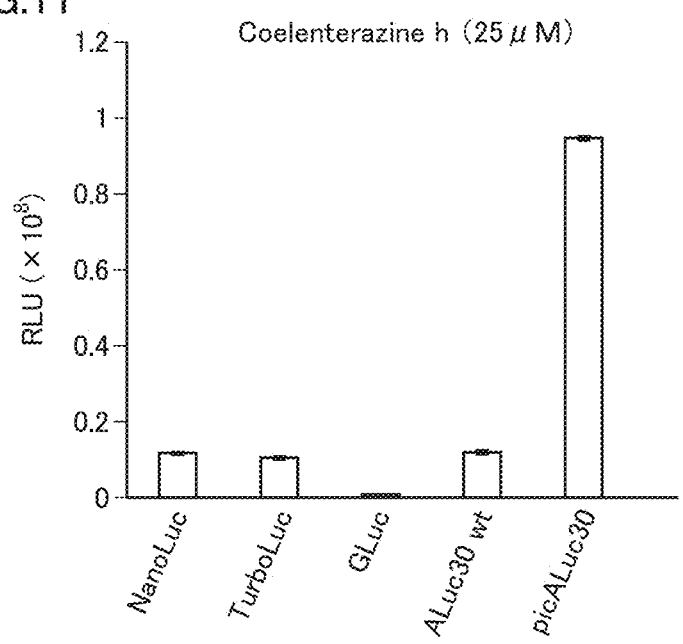
FIG. 11 is a graph of the emission value obtained when coelenterazine h (25 μM) was added as a substrate to luciferase in Experiment 5. The error bars represent ±1 SD (n=3).

The emission value was measured in the same manner as in Experiment 2 except that coelenterazine h was used as a substrate in a final concentration of 5 µM. The emission values were as follows: TurboLuc=ALuc30 wt>>NanoLuc>picALuc30>GLuc (FIG. 10). The emission value was measured in the same manner as in Experiment 2 except that coelenterazine h was used as a substrate in a final concentration of 25 µM. The emission values were as follows: picALuc30 >>NanoLuc=TurboLuc=ALuc30 wt>>GLuc (FIG. 11).

Figure 12:
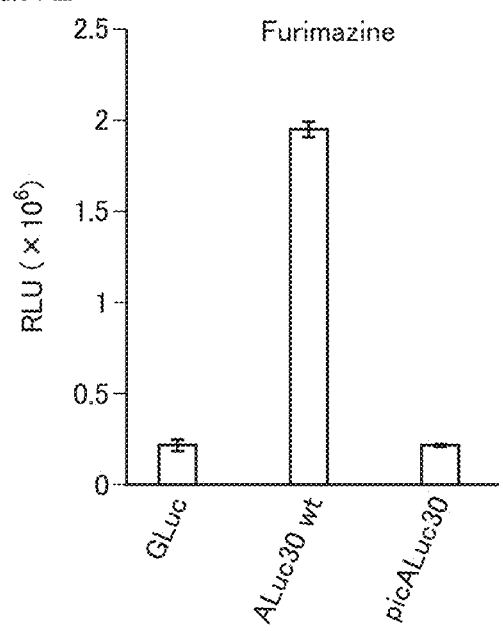
FIG. 12 is a graph of the emission value obtained when furimazine was added as a substrate to luciferase in Experiment 5. The error bars represent ±1 SD (n=3).
Figure 13:
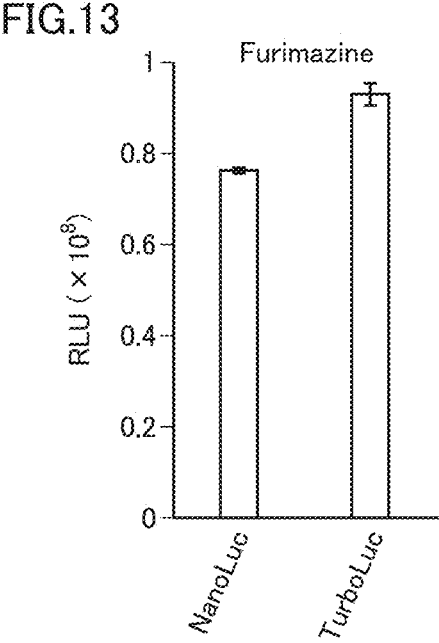
FIG. 13 is a graph of the emission value obtained when furimazine was added as a substrate to luciferase in Experiment 5. The error bars represent ±1 SD (n=3).

The emission value was measured in the same manner as in Experiment 2 except that furimazine, which was available from Promega as a NanoLuc substrate, was used as a substrate in the concentration recommended by the manufacturer. Emission was detected with GLuc, ALuc30 wt, and picALuc30, which was low as compared to NanoLuc and TurboLuc (FIG. 12 and FIG. 13). NanoLuc and TurboLuc exhibited high emission values, where the emission value of NanoLuc was the same as when coelenterazine or coelenterazine h was used (FIG. 13).

The above results suggested that coelenterazine and coelenterazine h were more suitable than furimazine as a substrate for picALuc30, and that secretion-expressed picALuc30, when reacted with substrate coelenterazine or coelenterazine h in a high concentration, exhibited an emission value that was equal to or higher than NanoLuc and TurboLuc.

<Experiment 6: Stability of Protein Terminus>

Figure 14:
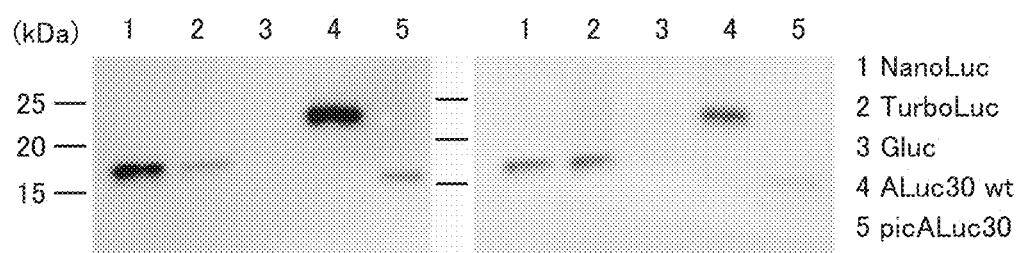
FIG. 14 shows Western blot detection of enzyme protein in supernatant in Experiment 6. The left shows flag-tag detection, and the right shows His-tag detection.

In the same manner as in Experiment 2, the plasmid was transfected into COS-7 cells and culture supernatant was collected. Flag-tag added to the N terminus of each secretion-expressed luciferase and His-tag added to the C terminus thereof were detected by Western blotting (SDS-PAGE, Mini-PROTEAN TGX Gel StainFree 4-15% (Bio-Rad)) (FIG. 14). The antibodies used were Anti 6×Histidine, Monoclonal Antibody (9C11), Peroxidase Conjugated (manufactured by FUJIFILM Wako Pure Chemical Corporation, 1:1000) and Monoclonal ANTI-FLAG (R) M2-Peroxidase (HRP) antibody produced in mouse, clone M2 (manufactured by Sigma-Aldrich, 1/1000), respectively, and detection was performed with Amesham Imager 680 (Cytiva). Flag-tag and His-tag on GLuc were lower than the detection limit. Signal intensity comparison between Flag-tag and His-tag on GLuc and TurboLuc indicated that Flag-tag on TurboLuc gave a low detection value and its N terminus was lost. In contrast, ALuc30 wt and picALuc30 had their both termini remaining, and showed high stability as compared to GLuc and TurboLuc.

<Experiment 7: Measurement of Specific Activity>

Figure 15:
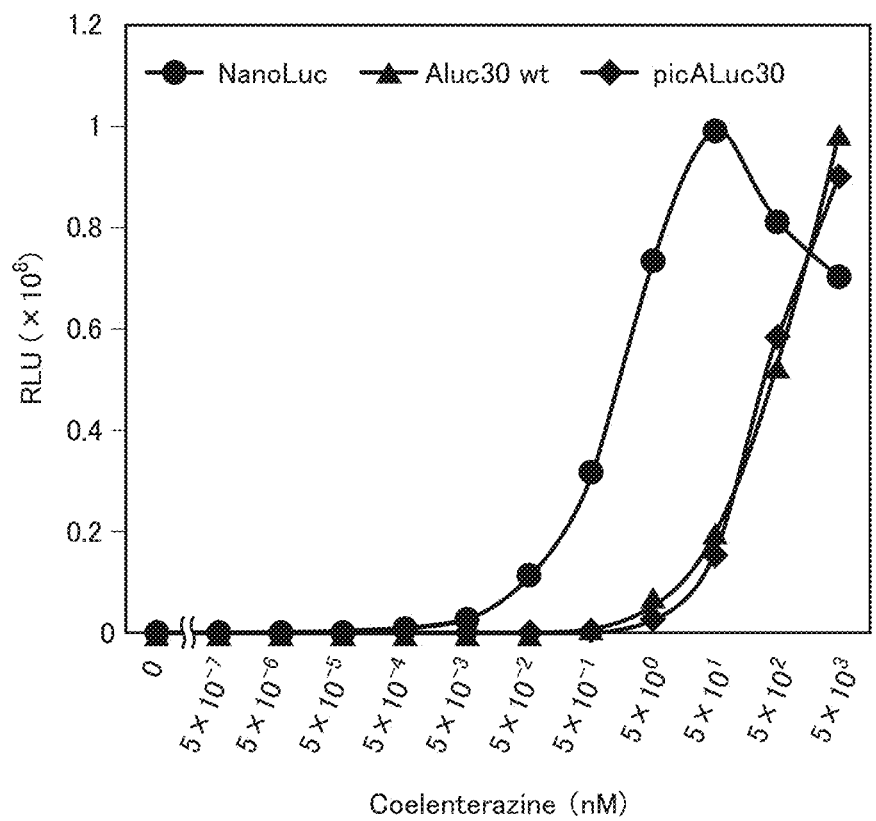
FIG. 15 is a graph of specific activity obtained when coelenterazine was added as a substrate to luciferase in Experiment 7.
Figure 16:
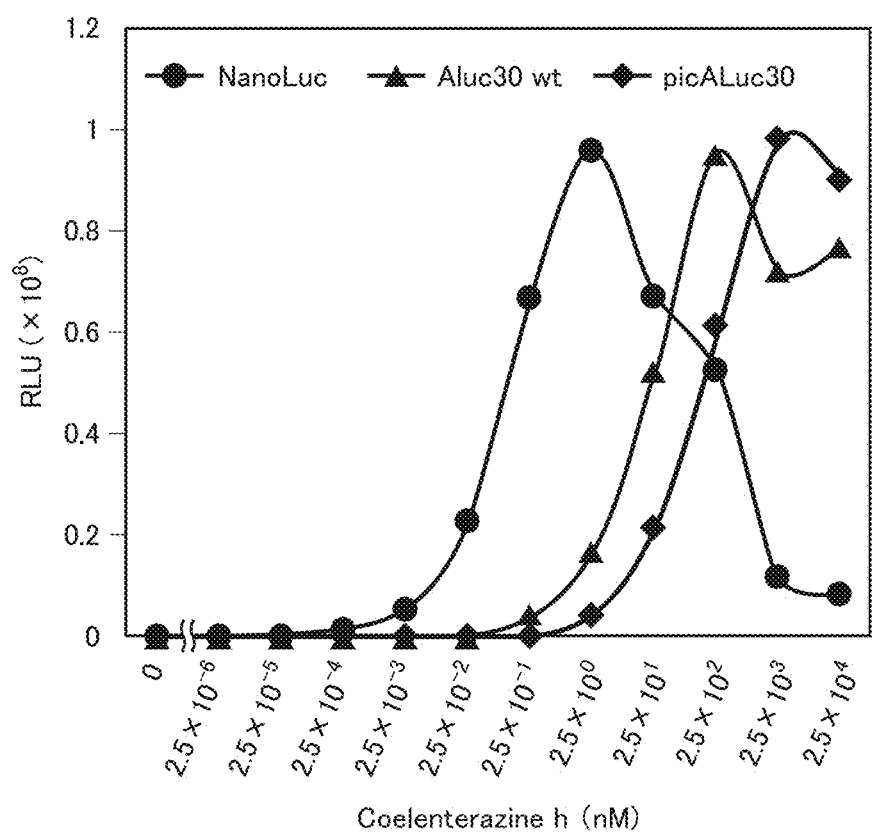
FIG. 16 is a graph of specific activity obtained when coelenterazine h was added as a substrate to luciferase in Experiment 7.

The specific activities of NanoLuc, ALuc30 wt, and picALuc30 were measured, with their enzyme concentrations adjusted based on the Western blot signal intensity obtained in Experiment 6. When coelenterazine or coelenterazine h was reacted as a substrate, the specific activity of ALuc was the same as the specific activity of picALuc (FIG. 15 and FIG. 16). ALuc30 wt and picALuc30 had the same maximum emission value as NanoLuc, indicating that they had high emission activities.

Figure 17:
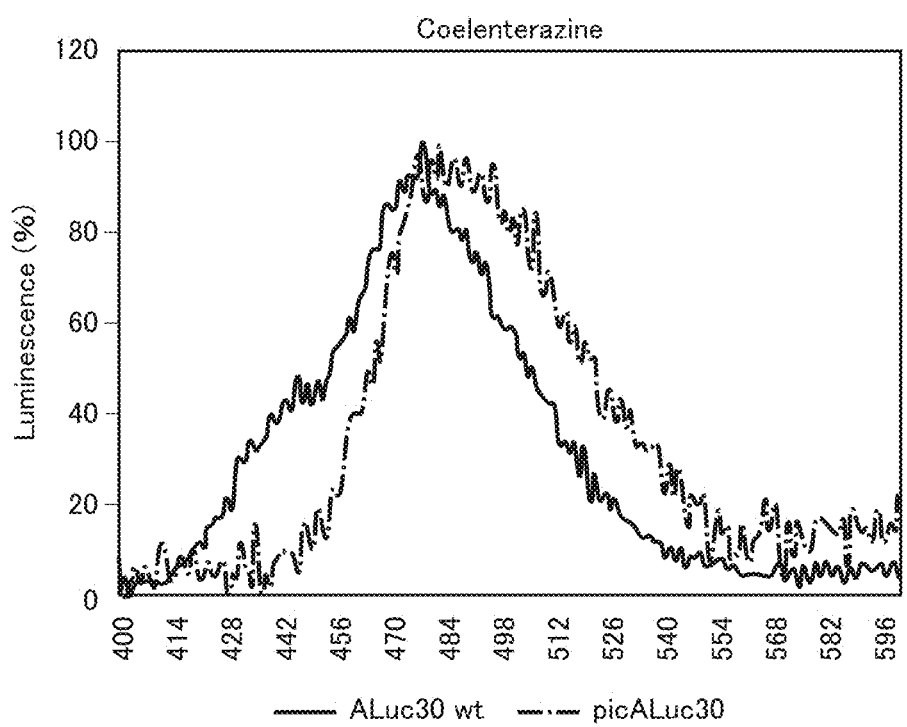
FIG. 17 shows the emission spectrum obtained when coelenterazine was added as a substrate to luciferase in Experiment 8.
Figure 18:
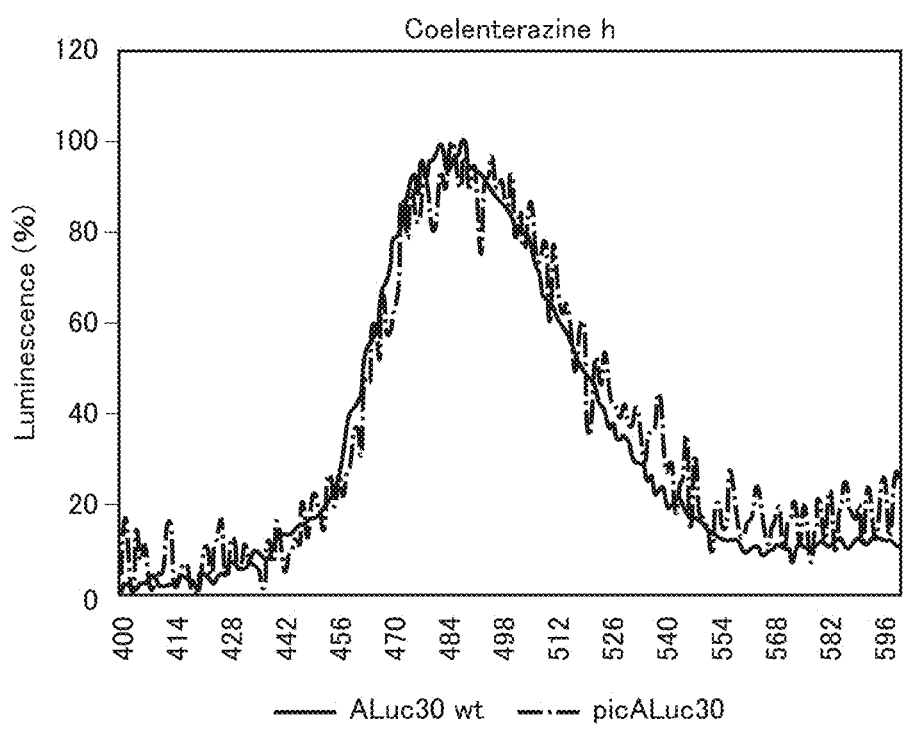
FIG. 18 shows the emission spectrum obtained when coelenterazine h was added as a substrate to luciferase in Experiment 8.

<Experiment 8: Measurement of Emission Spectrum> picALuc30 showed a wavelength peak at 482 nm when reacted with coelenterazine (FIG. 17), and at 488 m when reacted with coelenterazine h (FIG. 18). picALuc30 showed a wavelength peak approximately the same as ALuc30 wt. The emission spectrum had a characteristic wider tail on the longer wavelength side than on the shorter wavelength side.

<Experiment 9: Investigation of Thermal Stability>

Figure 19:
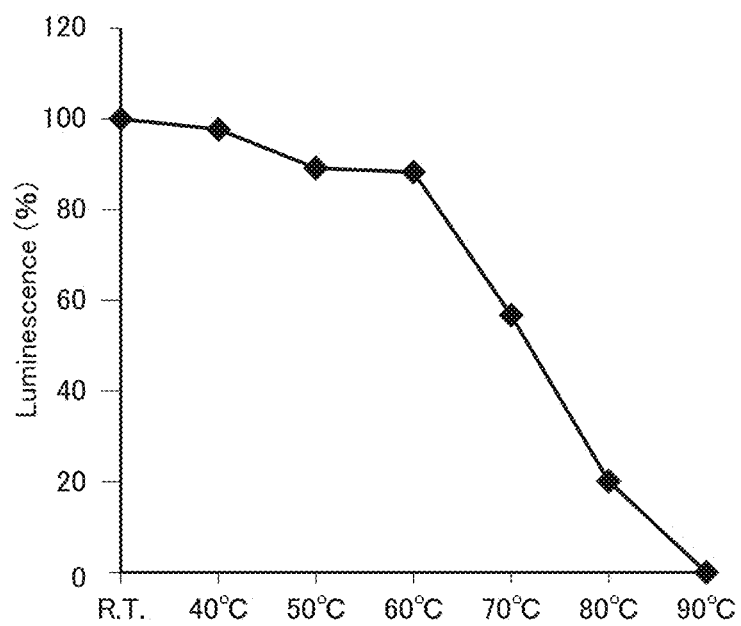
FIG. 19 is a graph of the post-heat-treatment emission value of secretion-expressed picALuc in Experiment 9.

In the same manner as in Experiment 2, the plasmid was transfected into COS-7 cells and the medium was collected. The culture supernatant containing picALuc30 was incubated for 10 minutes at room temperature (25° C.), 40° C., 50° C., 60° C., 70° C., 80° C., or 90° C., and then the emission value was measured. Results showed that 80% or more of the activity remained after 10-minute incubation at 50° C. or 10-minute incubation at 60° C., and 50% or more remained after 10-minute incubation at 70° C. (FIG. 19), indicating a sufficient level of practical utility.

<Experiment 10: Luciferase Expression in *Escherichia coli*>

(1) A DNA sequence coding for picALuc30 was inserted into a pET32 vector to prepare a plasmid. Transformation was carried out into *Escherichia coli* SHuffle T7 express lysY (New England Biolab).

(2) *Escherichia coli* from (1) was inoculated into an LB plate (containing 100 μg/μL of ampicillin).

(3) Next day, one colony was taken out, and cultured with shaking overnight at 30° C. in a test tube containing 2 mL of LB medium (containing 100 μg/μL of ampicillin).

(4) 1 mL of (3) was added to 100 mL of LB medium (containing 100 μg/μL of ampicillin), followed by shaking culture at 30° C. in a 500-mL flask until the absorbance $OD_{600}$ reached about 0.4.

(5) When the absorbance $OD_{600}$ reached about 0.4, 40 μL of 1-M isopropyl-β-thiogalactopyranoside was added, followed by overnight culture at 16° C.

(6) The bacterial cells were collected, followed by purification of the protein using HisTALON Buffer Set and TALON Metal Affinity Resin (both from Takara Bio Inc.). From 100 mL of the medium, 1.7 mg of picALuc30 was obtained.

Figure 20:
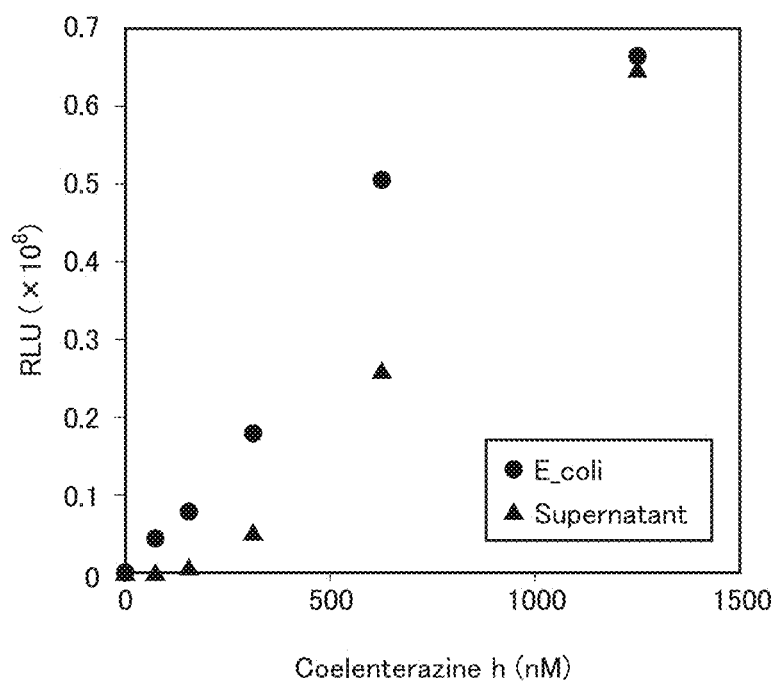
FIG. 20 is a graph of the emission values of picALuc that was secretion-expressed and picALuc that was expressed in *Escherichia coli* in Experiment 10.
Figure 21:
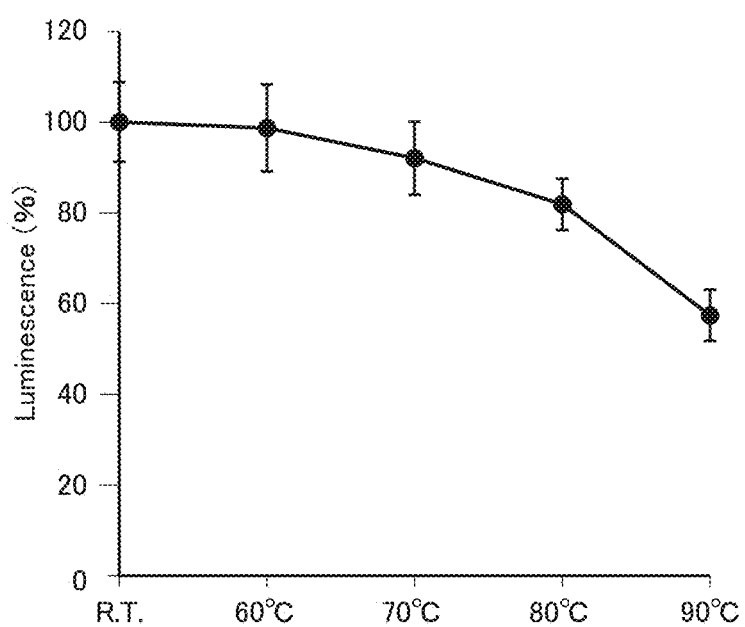
FIG. 21 is a graph of the post-heat-treatment emission value of picALuc expressed in *Escherichia coli* in Experiment 10. The error bars represent ±1 SD (n=3).

Specific activity was measured with the concentrations adjusted by way of Western blotting, and results showed that the specific activity of picALuc30 secretion expressed by COS-7 cells was approximately the same as the specific activity of picALuc30 prepared in *Escherichia coli* (FIG. 20). It indicates that picALuc30 can be not only secretion-expressed from mammalian cells but also expressed in *Escherichia coli*, and also a large-scale production is possible.

picALuc30 purified from *Escherichia coli* was incubated for 10 minutes at room temperature (25° C.), 60° C., 70° C., 80° C., or 90° C., followed by measurement of the emission value (FIG. 21). picALuc30 expressed in *Escherichia coli* lost little activity after 10-minute incubation at 60° C.; 90% or more of the activity remained after 10-minute incubation at 70° C., and 80% or more of the activity remained after 10-minute incubation at 80° C., indicating its excellent thermal stability.

<Experiment 11: BRET Molecular Probe>

Figure 22:
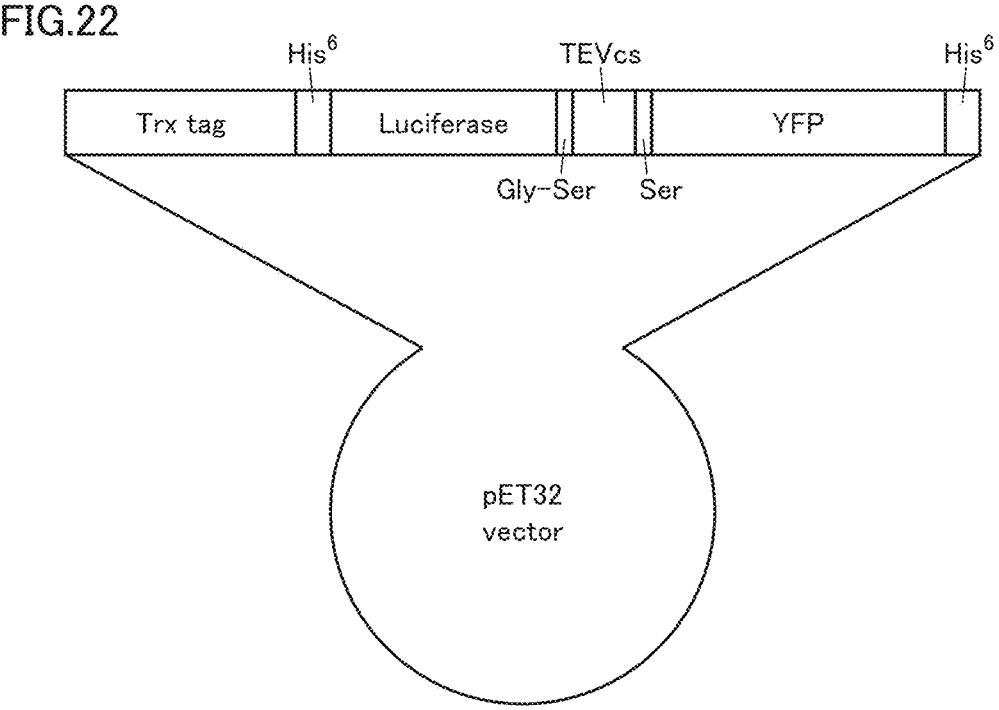
FIG. 22 shows a plasmid map used in Experiment 11.
Figure 23:
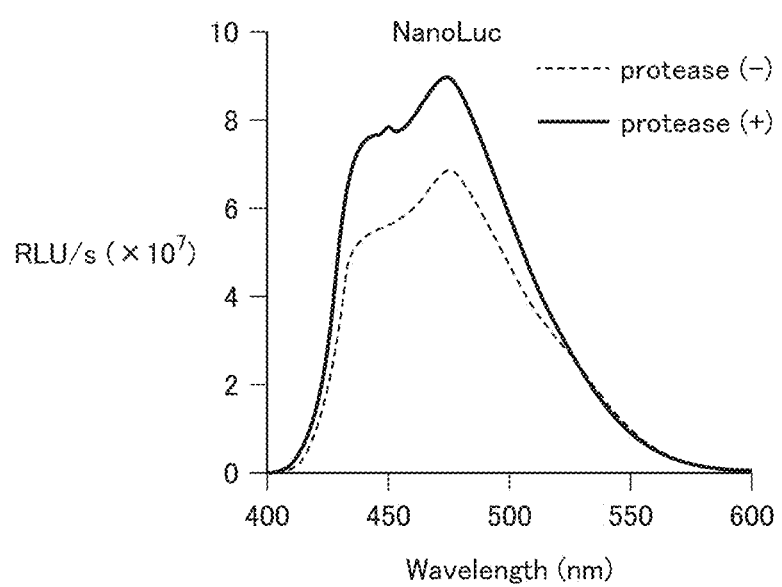
FIG. 23 shows the spectrum of a fusion protein composed of NanoLuc and YFP with addition of substrate coelenterazine h in Experiment 11.
Figure 24:
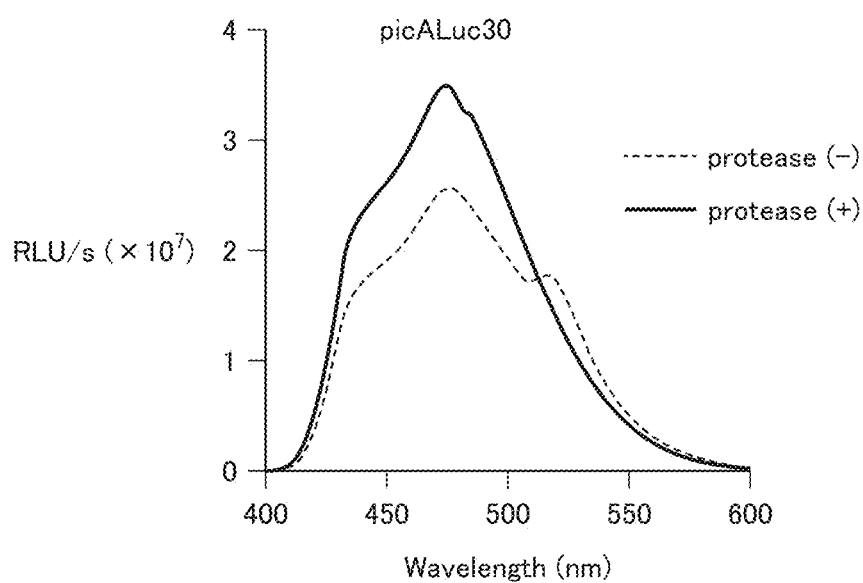
FIG. 24 shows the spectrum of a fusion protein composed of picALuc30 and YFP with addition of substrate coelenterazine h in Experiment 11.

Into pET32 vector, luciferase (NanoLuc or picALuc30)-Gly-Ser-(TEV protease recognition sequence (Glu-Asn-Leu-Tyr-Phe-Gln-Ser))-Ser-YFP was inserted (FIG. 22). By using this plasmid, protein expression and purification were carried out in the same manner as in Experiment 10. The fusion protein was subjected to reaction overnight at 30° C. with TEV protease (Cosmo Bio Co., Ltd.). As a control, a solution with no protease added was used. The protease-treated protein was diluted in 40-nM PBS, followed by reaction with substrate coelenterazine h (500 nM). The luciferase wavelength peak was detected at about 488 nm, and the YFP wavelength peak was detected at about 527 nm. The spectrum obtained with NanoLuc as luciferase is shown in FIG. 23, and the spectrum obtained with picALuc30 as luciferase is shown in FIG. 24.

Figure 25:
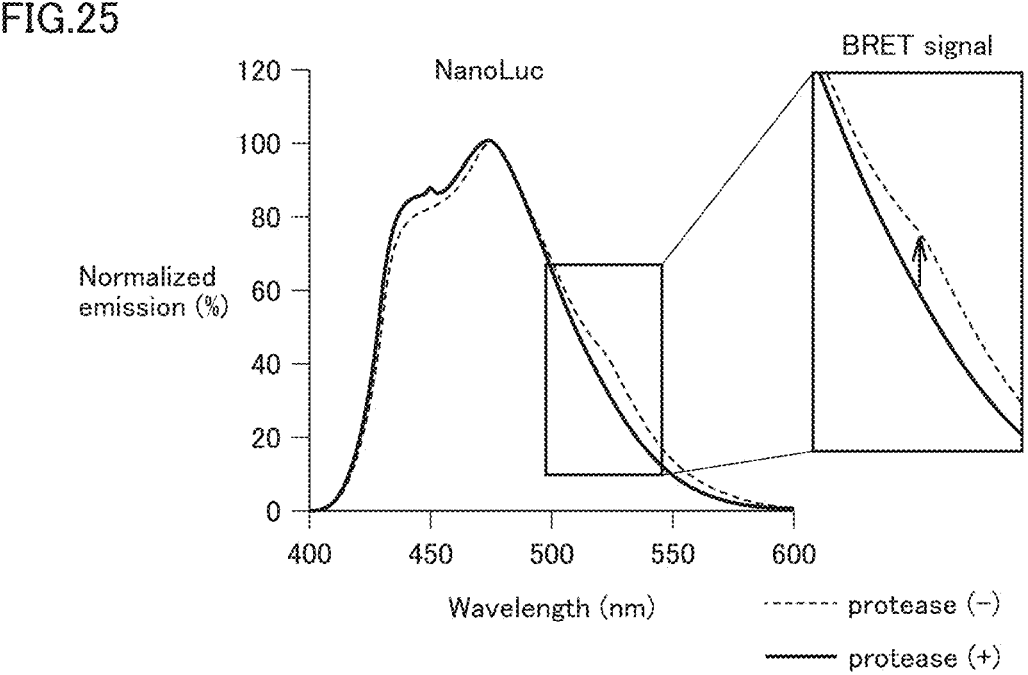
FIG. 25 shows the BRET signal of a fusion protein composed of NanoLuc and YFP in Experiment 11.
Figure 26:
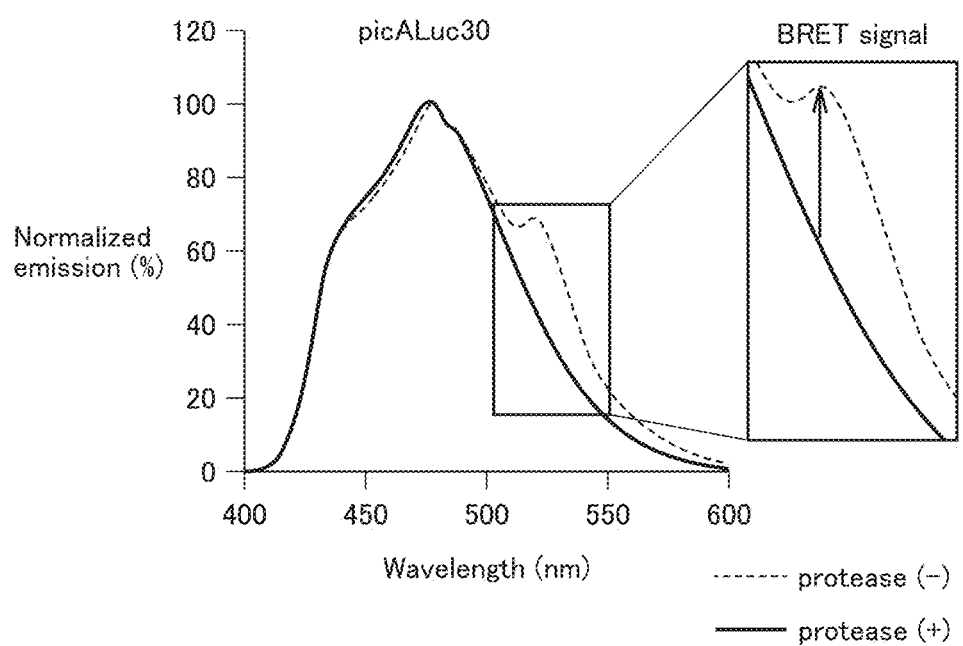
FIG. 26 shows the BRET signal of a fusion protein composed of picALuc30 and YFP in Experiment 11.

The BRET ratio was calculated, with the maximum NanoLuc emission value defined as 100%. Results showed that the BRET ratio of the NanoLuc-containing probe was 26% (FIG. 25) and the BRET ratio of the picALuc30-containing probe was 44% (FIG. 26). The BRET efficiency is inversely proportional to the sixth power of the distance between the luciferase and the fluorescent protein. It seems that ALuc30 had a higher BRET ratio than NanoLuc because picALuc was smaller than NanoLuc. It was suggested that the polypeptide according to the present invention is useful as a BRET molecular probe.

[Aspects]

As will be appreciated by those skilled in the art, the above-described example embodiments and Examples are specific examples of the below aspects.

(Item 1)

A polypeptide with luciferase activity comprising an amino acid sequence (A) or (B):

(A) an amino acid sequence as set forth in SEQ ID NO: 1 with deletion of amino acid residues at positions 1 to 69 and 204 to 221; or (B) an amino acid sequence as set forth in SEQ ID NO: 1 with deletion of amino acid residues at positions 1 to 69 and deletion or substitution of at least one of amino acid residues at positions 146 to 156.

The polypeptide according to Item 1 makes it possible to obtain a small luciferase that retains emission activity.

(Item 2)

In the polypeptide according to Item 1, the amino acid sequence further comprises deletion of at least one of amino acid residues at positions 70 to 74 of the amino acid sequence as set forth in SEQ ID NO: 1.

The polypeptide according to Item 2 makes it possible to obtain a smaller luciferase that retains emission activity.

(Item 3)

The polypeptide according to Item 1 or 2 comprises any one of sequences (a) to (c):

(a) an amino acid sequence as set forth in any one of SEQ ID NOs: 51 to 56;

(b) an amino acid sequence having at least 85% identity to an amino acid sequence as set forth in any one of SEQ ID NOs: 51 to 56; or (c) an amino acid sequence as set forth in any one of SEQ ID NOs: 51 to 56 with deletion, substitution, insertion, or addition of one or several amino acid residues.

The polypeptide according to Item 3 makes it possible to obtain a luciferase with a high emission activity.

(Item 4)

The polypeptide according to any one of Items 1 to 3 preserves at least 80% of its activity after heat treatment at a temperature of 50° C. for 10 minutes.

The polypeptide according to Item 4 makes it possible to obtain a luciferase with a high thermal stability.

(Item 5)

The polypeptide according to any one of Items 1 to 4 has a luciferase activity that shows:

an emission wavelength peak from 470 nm to 490 nm when coelenterazine is used as a substrate; or an emission wavelength peak from 470 nm to 490 nm when coelenterazine h is used as a substrate.

The polypeptide according to Item 5 has its emission spectrum shifted to a longer wavelength, and therefore the light transmits through a living body very well, giving an excellent detection sensitivity. Moreover, the polypeptide according to Item 5 is suitable for live imaging.

(Item 6)

A nucleic acid coding for the polypeptide according to any one of Items 1 to 5.

The nucleic acid according to Item 6 makes it possible to produce the polypeptide according to any one of Items 1 to 5.

(Item 7)

A vector comprising the nucleic acid according to Item 6.

The vector according to Item 7 makes it possible to easily amplify and retain the nucleic acid according to Item 6. Moreover, by using the vector according to Item 7, it is possible to produce the polypeptide according to any one of Items 1 to 5.

(Item 8)

A transformed cell into which the nucleic acid according to Item 6 has been introduced.

The transformed cell according to Item 8 is capable of expressing a luciferase. The luciferase may be secreted into the supernatant.

(Item 9)

A reporter protein formed of the polypeptide according to any one of Items 1 to 5.

The polypeptide according to any one of Items 1 to 5 may be used as a reporter protein.

(Item 10)

A reporter analysis method that uses the reporter protein according to Item 9.

The reporter analysis method according to Item 10 makes it possible to efficiently detect the behavior of a target protein and/or a target gene. In the reporter analysis method according to Item 10, instead of a luciferase used in a known reporter analysis method, the polypeptide according to any one of Items 1 to 5 may be used as a luciferase.

(Item 11)

A fusion protein comprising the polypeptide according to any one of Items 1 to 5 and a target protein or a protein capable of binding a target protein.

The fusion protein according to Item 11 makes it possible to detect the behavior of a target protein by way of luminescence.

(Item 12)

A vector comprising a nucleic acid coding for the fusion protein according to Item 11.

The vector according to Item 12 makes it possible to easily amplify and retain a nucleic acid coding for the fusion protein according to Item 11. By using the vector according to Item 12, it is possible to easily produce the fusion protein according to Item 11.

(Item 13)

A bioluminescence resonance energy transfer (BRET) molecular probe comprising the polypeptide according to any one of Items 1 to 5 and a fluorescent substance.

The molecular probe according to Item 13 makes it possible to detect a protease and the like with a high sensitivity.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A polypeptide with luciferase activity comprising an amino acid sequence (A) or (B):
   (A) the amino acid sequence of SEQ ID NO: 1 with deletion of amino acid residues at positions 1 to 69 and 204 to 221; or
   (B) the amino acid sequence of SEQ ID NO: 1 with deletion of amino acid residues at positions 1 to 69 and deletion or substitution of at least one of amino acid residues at positions 146 to 156;
   wherein the polypeptide includes any one of sequences (a) to (c):
   (a) the amino acid sequence of any one of SEQ ID NOs: 51, 52 and 56;
   (b) an amino acid sequence having at least 85% identity to the amino acid sequence of any one of SEQ ID NOs: 51, 52 and 56; or
   (c) the amino acid sequence of any one of SEQ ID NOs: 51, 52 and 56 with deletion, substitution, insertion, or addition of 1 to 20 amino acid residues.

2. The polypeptide according to claim 1, wherein the amino acid sequence further comprises deletion of at least one of amino acid residues at positions 70 to 74 of the amino acid sequence as set forth in SEQ ID NO: 1.

3. The polypeptide according to claim 1, wherein at least 80% of the luciferase activity is preserved after heat treatment at a temperature of 50° C. for 10 minutes.

4. The polypeptide according to claim 1, wherein the luciferase activity shows:
   an emission wavelength peak from 470 nm to 490 nm when coelenterazine is used as a substrate; or
   an emission wavelength peak from 470 nm to 490 nm when coelenterazine h is used as a substrate.

5. A reporter protein formed of the polypeptide according to claim 1.

6. A fusion protein comprising the polypeptide according to claim 1 and a target protein or a protein capable of binding a target protein.

7. A bioluminescence resonance energy transfer (BRET) molecular probe comprising the polypeptide according to claim 1 and a fluorescent substance.

* * * * *